United States Patent
Reinhard et al.

(10) Patent No.: US 10,646,451 B2
(45) Date of Patent: *May 12, 2020

(54) GM3 FUNCTIONALIZED NANOPARTICLES

(71) Applicant: TRUSTEES OF BOSTON UNIVERSITY, Boston, MA (US)

(72) Inventors: Bjoern Markus Reinhard, Brookline, MA (US); Suryaram Gummuluru, Westwood, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/986,186

(22) Filed: May 22, 2018

(65) Prior Publication Data

US 2018/0296492 A1 Oct. 18, 2018

Related U.S. Application Data

(63) Continuation of application No. 15/304,127, filed as application No. PCT/US2015/024965 on Apr. 8, 2015, now Pat. No. 10,004,695.

(Continued)

(51) Int. Cl.
*A61K 9/51* (2006.01)
*A61K 9/127* (2006.01)
(Continued)

(52) U.S. Cl.
CPC .......... *A61K 9/5123* (2013.01); *A61B 5/055* (2013.01); *A61K 9/127* (2013.01); *A61K 9/1271* (2013.01); *A61K 9/1272* (2013.01); *A61K 9/5115* (2013.01); *A61K 9/5192* (2013.01); *A61K 47/543* (2017.08); *A61K 47/61* (2017.08); *A61K 47/6911* (2017.08); *A61K 47/6923* (2017.08); *A61K 47/6929* (2017.08); *B82Y 5/00* (2013.01); *G01N 33/5005* (2013.01)

(58) Field of Classification Search
CPC ......... A61K 9/5123; A61K 9/127; B82Y 5/00
See application file for complete search history.

(56) References Cited

U.S. PATENT DOCUMENTS

| | | | |
|---|---|---|---|
| 2013/0028962 A1 | 1/2013 | Zhang et al. | |
| 2013/0204121 A1 | 8/2013 | Andresen et al. | |
| 2014/0037736 A1* | 2/2014 | Shi | A61K 39/00 424/489 |

FOREIGN PATENT DOCUMENTS

| | | |
|---|---|---|
| WO | 2012/007567 A1 | 1/2012 |
| WO | 2013/092509 A1 | 6/2013 |
| WO | 2013092509 * | 6/2013 |

OTHER PUBLICATIONS

IP et al., "Phospholipid membrane encapsulation of nanoparticles for surface-enhanced Raman scattering", Langmuir, 27(11):7024-33 (2011).

(Continued)

*Primary Examiner* — Carlos A Azpuru
(74) *Attorney, Agent, or Firm* — Nixon Peabody LLP

(57) ABSTRACT

Embodiments disclosed herein relates to ganglioside GM3-containing mixed lipids nanoparticles having an overall size between 60-100 nm, the making thereof and the uses. The nanoparticles selectively targeted to CD169+ expressing cells such as dendritic cells and macrophage. The nanoparticles are endocytosed by the CD169+ expressing cells.

17 Claims, 7 Drawing Sheets

Specification includes a Sequence Listing.

Related U.S. Application Data

(60) Provisional application No. 61/980,175, filed on Apr. 16, 2014.

(51) Int. Cl.

| | | |
|---|---|---|
| *B82Y 5/00* | (2011.01) | |
| *A61B 5/055* | (2006.01) | |
| *G01N 33/50* | (2006.01) | |
| *A61K 47/69* | (2017.01) | |
| *A61K 47/61* | (2017.01) | |
| *A61K 47/54* | (2017.01) | |

(56) References Cited

OTHER PUBLICATIONS

Izquierdo-Useros et al., "Sialyllactose in viral membrane gangliosides is a novel molecular recognition pattern for mature dendritic cell capture of HIV-1", PLoS Biol, 10(4):e1001315 (2012).

Moghimi et al., "Long-circulating and target-specific nanoparticles: theory to practice", Pharmacol Rev, 53(2):283-318 (2001).

Puryear et al., "HIV-1 incorporation of host-cell-derived glycosphingolipid GM3 allows for capture by mature dendritic cells." PNAS 109(19):7475-7480 (2012).

Yang et al., "Evidence for patchy lipid layers on gold nanoparticle surfaces", Langmuir, 28(12):5404-16 (2012).

Yu et al., "Glycosphingolipid-functionalized nanoparticles recapitulate CD169-dependent HIV-1 uptake and trafficking in dendritic cells" Nat Commun, 5:4136 (2014).

Yu et al., "Plasmonic optical nanoparticles probe the nano-bio interface", SPIE 3pp. (2014).

\* cited by examiner

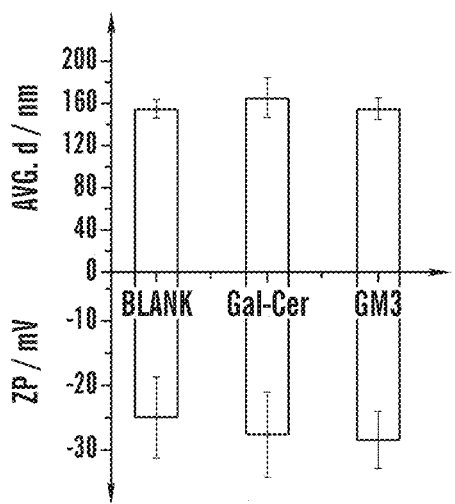 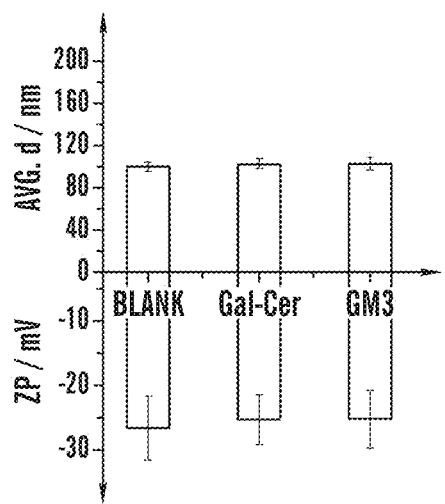
FIG. 2A    FIG. 2B
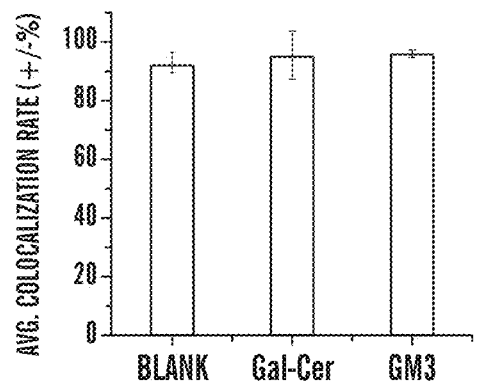 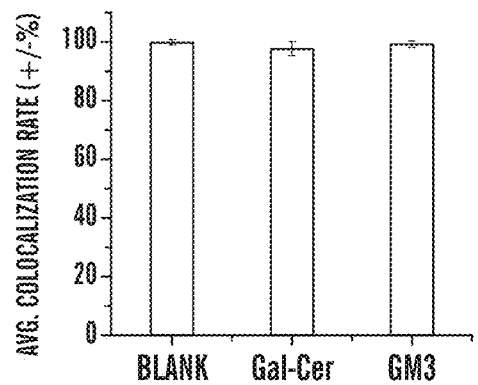
FIG. 2C    FIG. 2D
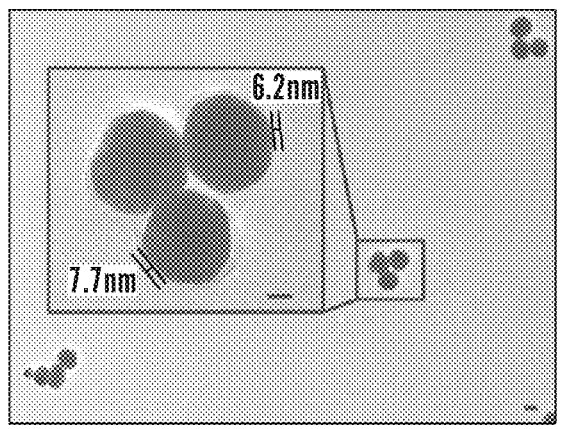 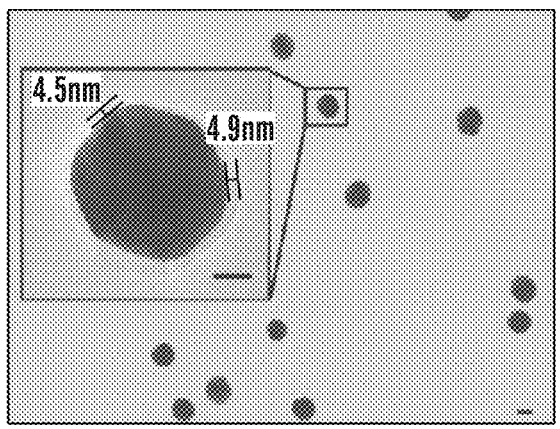
FIG. 2E    FIG. 2F

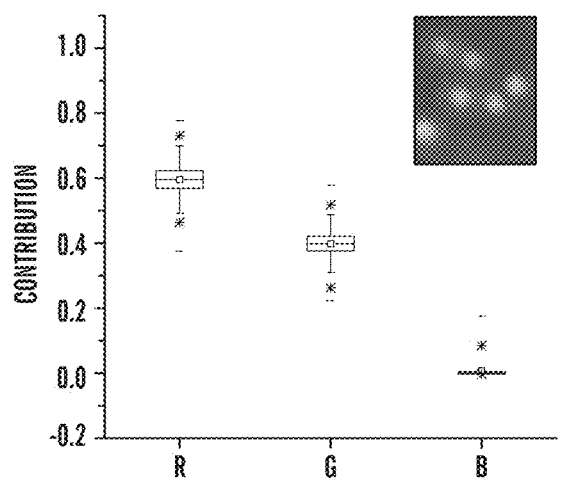
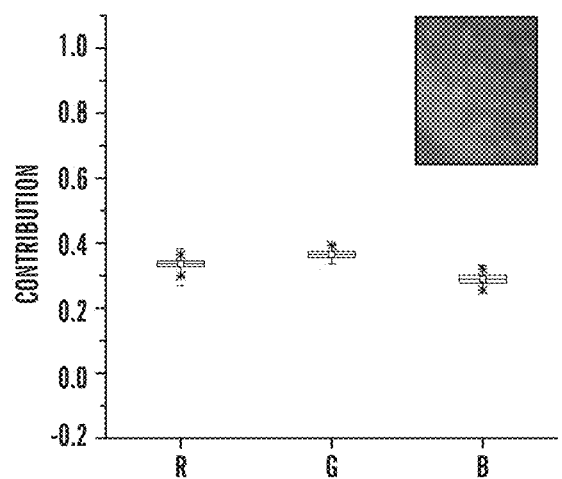
*FIG. 3A*  *FIG. 3B*
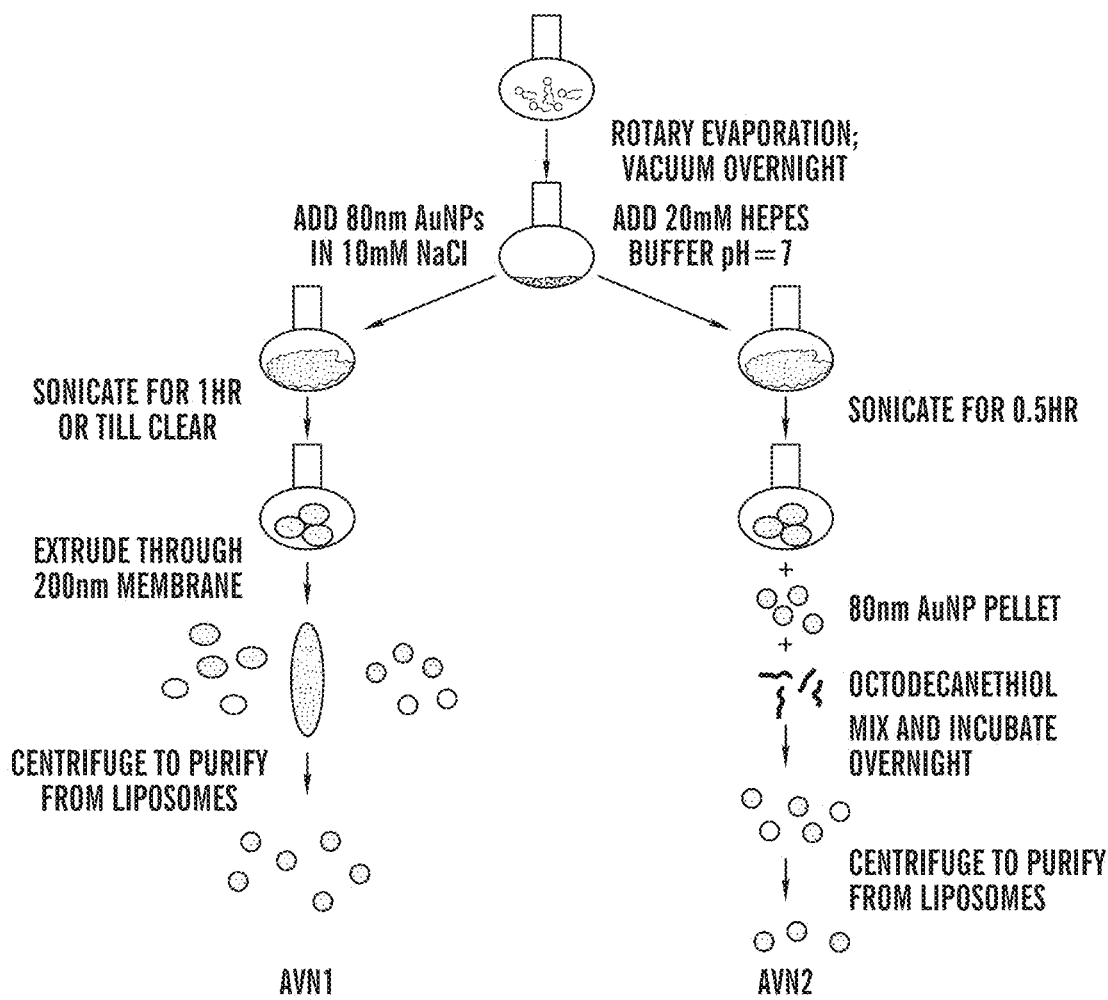
*FIG. 4*

GM3 FUNCTIONALIZED NANOPARTICLES

CROSS REFERENCE TO RELATED APPLICATION

This application is a continuation of U.S. patent application Ser. No. 15/304,127, filed Oct. 14, 2016, now U.S. Pat. No. 10,004,695, which is a 35 U.S.C. § 371 National Phase Entry of the International Application No. PCT/US2015/024965 filed Apr. 8, 2015, which designates the U.S. and which claims benefit under 35 U.S.C. § 119(e) of the U.S. provisional application No. 61/980,175 filed Apr. 16, 2014, the contents of each of which are incorporated herein by reference in its their entirety.

GOVERNMENT SUPPORT

This invention was made with Government support under Grant Numbers AI104393 and AI064099 awarded by the National Institutes of Health. The Government has certain rights in the invention.

SEQUENCE LISTING

The instant application contains a Sequence Listing which has been submitted electronically in ASCII format and is hereby incorporated by reference in its entirety. The ASCII copy, created on Apr. 8, 2015, is named 701586-080931-PCT_SL.txt and is 1,156 bytes in size.

FIELD OF THE DISCLOSURE

The disclosure relates to nanoparticles coated with lipids. Specifically, nanoparticles coated externally with a mixed lipid composition. By varying the mixed lipid composition, it is possible to strategically direct the nanoparticles to specific target of desire.

BACKGROUND

Virions are endogenous smart nanoparticles (NPs) that are evolutionarily optimized to achieve efficient reproduction in host cells. The viral surface plays a crucial role in establishing successful infection since it facilitates the binding of virus particles to the host cell and the subsequent initiation of an uptake program that results in the delivery of the viral genetic content to the intracellular virus replication machinery. Many of these interactions are facilitated by specific virus-encoded proteins, such as gp120 (HIV-1 envelope glycoprotein) in the case of productive (or cis) HIV-1 infection of CD4+ T cells and macrophages. There is, however, a growing body of evidence that some infection mechanisms also depend critically on the composition of the viral lipidome. In particular, host derived glycosphingolipids (GSLs) incorporated into the virion play a central role for HIV-1 uptake and transmission by mature DCs, a DC-mediated HIV-1 trans-infection pathway. The GSL that mediates the glycoprotein-independent interactions between HIV-1 and mature DCs was identified as monosialodihexosylganglioside (GM3),8,11 and the type 1 interferon inducible Siglec1, CD169, has been identified as the corresponding receptor that recognizes GM3 present in the membrane of HIV-1 particles. Furthermore, virus particles captured by CD169 in a GM3-dependent manner are sequestered in non-lysosomal compartments, and upon initiation of DC-T cell contacts transferred to the DC-T cell synaptic junction, termed "virological synpase". Since the cytoplasmic tail of CD169 lack any known endocytic motifs, many details of the mechanisms underlying CD169-mediated HIV-1 uptake and subsequent trafficking to DC-T cell virological synapses remain currently unclear. The latter is—at least in part—due to experimental complications associated with a systematic investigation of the role of individual host-encoded viral surface functionalities in trans-infection. One particular challenge is that the compositional complexity of both cellular and viral surfaces gives rise to a multitude of potential interactions that can be both physical and chemical in nature and which are difficult to decouple in conventional virus models. A second complication is that mechanistic information about the cellular machinery orchestrating the virus trafficking is best obtained by single virus trafficking. This approach requires, however, bright labels that facilitate an optical tracking with high temporal resolution, ideally without limitation in maximum observation time.

Different virus model systems have been developed for delivery purposes as well as for structural or mechanistic studies. Successful realizations include virus like particles (VLPs), virus-based nanoparticles, liposomes, and hybrid systems in which biomolecules are combined with inorganic nanoparticles to reproduce viral functionality. None of the systems implemented so far, however, fulfill all the specific requirements with regard to size, transducing capability, surface composition, and engineerability to characterize the mechanistic role of GM3 in the membrane of the HIV-1 virion. For instance, HIV-1 Gag VLPs, which are common tools for characterizing the role of non-virus encoded host cell surface functionalities, are immature virion cores wrapped in a lipid bilayer derived upon budding from a virus-producer cell and can contain host-derived membrane glycoproteins in addition to a broad range of different (glyco)lipids. These additional groups can compete or interfere with the biological functionality of GM3. Clearly, there is a desire for better designs of engineered virion mimics.

SUMMARY

The monosialoldihexosylganglioside GM3 is a host-derived glycosphingolipid incorporated in the membrane of human immunodeficiency virus type-1 (HIV-1) particles that can elicit glycoprotein-independent interactions between HIV-1 and Siglec1/CD169 expressed on dendritic cells (DCs). A selective characterization of GM3 mediated virus binding to CD169 and uptake calls for model systems that are free of viral envelope glycoproteins or other host-derived glycolipids and glycoproteins.

The inventors harnessed the specific functionality of GM3 as a potential viral surface ligand to design an engineered virion mimic. The inventors demonstrated with artificial virus nanoparticles (AVNs), which contain a membrane of defined composition wrapped around a metal nanoparticle core, that the recognition of GM3 through cell-surface CD169 is sufficient to facilitate a specific binding of AVNs and virus particles to host cells. Unlike GM3 containing liposomes that are known, the GM3 functionalized AVNs induce a temporo-spatial distribution that is distinctly different from conventional NP endocytosis and that results in an enrichment of AVNs in peripheral, tetraspanin-positive, non-lysosomal compartments.

The engineered virion mimic is a GM3-dependent but envelope glycoprotein-independent viral binding with self-assembled artificial virus nanoparticles (AVNs). These biomimetic nanosystems contain a membrane of defined composition wrapped around a solid metal core. The inventors demonstrate that capture of GM3-containing AVNs by CD169-expressing HeLa cells or mature DCs induces a spatial sequestration and enrichment of AVNs non-lysosomal, tetraspanin-positive compartments. This spatial distribution is reminiscent of CD169-dependent HIV-1 sequestration in DCs and highlights GM3-CD169 binding as an envelope glycoprotein-independent signal for sequestration and preservation of virus infectivity.

Accordingly, in one embodiment, the disclosure here provides a nanoparticle comprising: (a) a core having a largest diameter between 50-90 nm; (b) a coating layer encasing the core; and (c) a ganglioside GM3-containing mixed lipid layer comprising of dipalmitoylphosphatidylcholine (DPPC), cholesterol, phosphatidylserine (PS), and aNeu5Ac(2-3)bDGalp(1-4)bDGlcp(1-1)Cer (GM3); wherein the ganglioside GM3-mixed lipid layer is exterior of the coating layer and is integrated into the coating layer, and wherein the nanoparticles have an overall particle size between 60-100 nm.

In another embodiment, the disclosure here provides a method of delivering a nanoparticle into a cell comprising (a) adding a nanoparticle of described herein to a CD169-expressing eukaryotic cell under conditions that permit the nanoparticle to be endocytosed into the CD169-expressing eukaryotic cell, and (b) waiting for a sufficient time for endocytosis to occur.

In one embodiment, the disclosure here provides a pharmaceutical composition comprising a nanoparticle described herein in a physiologically acceptable carrier.

In one embodiment, the disclosure here provides a method of making a nanoparticle described herein comprising: (a) contacting a core nanoparticle with a coating layer material to coat the particle; (b) adding the coated core nanoparticle to a ganglioside GM3 containing mixed lipid solution; (c) sonicating the contacted mixture of step (b) for a period of time; (d) extruding the particles from step (c) through a membrane with a pore size of about 100-200 nm; and (e) collecting the extruded nanoparticles from the membrane.

In one embodiment, the disclosure here provides a method of making a nanoparticle described herein comprising: (a) adding a thiolated lipid to a core particle to coat the particle; (b) sonicating a ganglioside GM3 containing mixed lipid solution for a period of time to form liposomes; (c) adding the thiolaled lipid coated particle of step (a) to the liposomes of step (b); and (d) collecting nanoparticles formed.

In another embodiment, the disclosure here provides a method of studying the interaction between CD169+ dendritic cells or macrophage and CD4+ T cells comprising: (a) contacting a CD169+ dendritic cell or macrophage with a nanoparticle described herein; (b) allowing the nanoparticle to be taken up into the CD169+ dendritic cell or macrophage; contacting the cell of step (b) with a CD4+T cells; and observing the interaction between the CD169+ dendritic cell or macrophage and the CD4+ T cell.

In one embodiment of any one of the nanoparticle described, the core of the nanoparticle is a solid core. In another embodiment, the core is hollow. In another embodiment, the core comprises a perforated shell.

In one embodiment of any one of the nanoparticle described, the core is has a shape that is selected from the group consisting of ellipsoid, spherical, rod-like, octahedral, and cube-like.

In one embodiment of any one of the nanoparticle described, the core comprises a material selected from the group consisting of gold, silver, a gold alloy, a silver alloy, silica, mesoporous silica, polystyrene, and titania.

In one embodiment of any one of the nanoparticle described, the coating layer on the nanoparticle is a thiolated lipid.

In one embodiment of any one of the nanoparticle described, the thiolated lipid comprises long-chain thiol-terminated alkanes.

In one embodiment of any one of the nanoparticle described, the thiolated lipid is selected from the group consisting of octodecanethiol, hexadecane thiol, heptadecane thiol, and octadecane.

In one embodiment of any one of the nanoparticle described, the coating layer is a silane with long alkyl chains.

In one embodiment of any one of the nanoparticle described, wherein the silane is octadecylsilane.

In one embodiment of any one of the nanoparticle described, the coating layer is polyethylene glycol thiol.

In one embodiment of any one of the nanoparticle described, the ganglioside GM3 containing mixed lipid layer consists of 40%-60% of DPPC, 1,2-dimyristoyl-sn-glycero-3-phosphocholine (DMPC) or 1,2-Distearoyl-sn-glycero-3-phosphocholine (DSPC).

In one embodiment of any one of the nanoparticle described, the ganglioside GM3 containing mixed lipid layer consists of 40%-60% of a combination of two or more lipids selected from the group consisting of DPPC, DMPC and DSPC.

In one embodiment of any one of the nanoparticle described, the ganglioside GM3 containing mixed lipid layer consists of 40%-60% of cholesterol.

In one embodiment of any one of the nanoparticle described, the ganglioside GM3 containing mixed lipid layer consists of 0.5%-5% of PS.

In one embodiment of any one of the nanoparticle described, the ganglioside GM3 containing mixed lipid layer consists of 0.1%-6% of GM3.

In one embodiment of any one of the nanoparticle described, the ganglioside GM3 containing mixed lipid layer optionally contains 0.1%-6% of galactosylceramide (Gal-Cer).

In one embodiment of any one of the nanoparticle described, the ganglioside GM3 containing mixed lipid layer comprises of DPPC, cholesterol, PS, and GM3.

In one embodiment of any one of the nanoparticle described, the ganglioside GM3 containing mixed lipid layer consists of DPPC, cholesterol, PS, and GM3.

In one embodiment of any one of the nanoparticle described, the ganglioside GM3 containing mixed lipid layer consists essentially of DPPC, cholesterol, PS, and GM3.

In one embodiment of any one of the nanoparticle described, the ganglioside GM3 containing mixed lipid layer comprises of DPPC, cholesterol, PS, GM3 and Gal-Cer.

In one embodiment of any one of the nanoparticle described, the ganglioside GM3 containing mixed lipid layer consists of DPPC, cholesterol, PS, GM3 and Gal-Cer.

In one embodiment of any one of the nanoparticle described, the ganglioside GM3 containing mixed lipid layer consists essentially of DPPC, cholesterol, PS, GM3 and Gal-Cer.

In one embodiment of any one of the nanoparticle described, the ganglioside GM3 containing mixed lipid layer comprises of DMPC, cholesterol, PS, and GM3

In one embodiment of any one of the nanoparticle described, the ganglioside GM3 containing mixed lipid layer consists of DMPC, cholesterol, PS, and GM3.

In one embodiment of any one of the nanoparticle described, the ganglioside GM3 containing mixed lipid layer consists essentially of DMPC, cholesterol, PS, and GM3.

In one embodiment of any one of the nanoparticle described, the ganglioside GM3 containing mixed lipid layer comprises of DMPC, cholesterol, PS, GM3 and Gal-Cer.

In one embodiment of any one of the nanoparticle described, the ganglioside GM3 containing mixed lipid layer consists of DMPC, cholesterol, PS, GM3 and Gal-Cer.

In one embodiment of any one of the nanoparticle described, the ganglioside GM3 containing mixed lipid layer consists essentially of DMPC, cholesterol, PS, GM3 and Gal-Cer.

In one embodiment of any one of the nanoparticle described, the ganglioside GM3 containing mixed lipid layer comprises of DSPC, cholesterol, PS, and GM3

In one embodiment of any one of the nanoparticle described, the ganglioside GM3 containing mixed lipid layer consists of DSPC, cholesterol, PS, and GM3.

In one embodiment of any one of the nanoparticle described, the ganglioside GM3 containing mixed lipid layer consists essentially of DSPC, cholesterol, PS, and GM3.

In one embodiment of any one of the nanoparticle described, the ganglioside GM3 containing mixed lipid layer comprises of DSPC, cholesterol, PS, GM3 and Gal-Cer.

In one embodiment of any one of the nanoparticle described, the ganglioside GM3 containing mixed lipid layer consists of DSPC, cholesterol, PS, GM3 and Gal-Cer.

In one embodiment of any one of the nanoparticle described, the ganglioside GM3 containing mixed lipid layer consists essentially of DSPC, cholesterol, PS, GM3 and Gal-Cer.

In one embodiment of any one of the nanoparticle described, the nanoparticle comprises a second layer of ganglioside GM3 containing mixed lipid.

In one embodiment of any one of the nanoparticle described, the CD169-expressing eukaryotic cell is a Hela cell, a dendritic cell or a macrophage.

In one embodiment of any one of the nanoparticle described, the nanoparticle is sequestered within non-lysosomal tetraspanin-positive compartments of the CD169-expressing eukaryotic cell.

BRIEF DESCRIPTION OF THE DRAWINGS

FIG. 1a shows the scheme of HIV-1 structure. HIV-1 is composed of a host derived lipid bilayer membrane wrapped around a protein matrix core that contains the viral RNA. Major lipid components of the viral membrane are included. The viral membrane contains additional lipids, including GM3, albeit with significantly lower concentration. Another membrane component is the virus-encoded glycoprotein gp120.

FIG. 1b shows the scheme of minimalistic artificial model systems, AVN1 (left) and AVN2 (right). Both AVNs are assembled from 80 nm Au NP cores and comprise a self-assembled lipid membrane. AVN1 contains a lipid bilayer, whereas AVN2 contains a lipid monolayer anchored in a self-assembled octodecanethiol layer. The thiol covalently attaches to the NP surface.

FIGS. 2a-2f show the characterization of two embodiments of NPs, named AVNs.

FIGS. 2a and 2b show the Zeta potential and average hydrodynamic radius of (FIG. 2a) AVN1 and (FIG. 2b) AVN2 without glycosphingolipids (Blank) or containing 3% Gal-Cer, or 3% GM3. The presented data were obtained from three independent experiments.

FIGS. 2c and 2d show the tabulated average colocalization statistics for (FIG. 2c) AVN1 and (FIG. 2d) AVN2 collected from darkfield image and fluorescence images that were subsequently overlay over each other. 1000 particles were evaluated for each colocalization statistics.

FIGS. 2e and 2f show the representative magnified TEM image of selected AVNs of (FIG. 2e) AVN1 and (FIG. 2f) AVN2, showing a distinct corona formed by the self-assembled lipids around the NPs. Scale bars are 20 nm FIGS. 3a-3b show the binding of AVNs to HeLa/CD169 cells is GM3 specific. The graphs show the relative intensity distribution on the red (R), green (G), and blue (B) color channels of a digital camera for an AVN-bound cell surface (FIG. 3a) and (FIG. 3b) for control cell surface void of AVNs. Scale bars are 10 μm. GM3 binding specificity studies were independently repeated >3 times.

FIG. 4 shows the scheme of the fabrication procedures for two embodiments of NPs, the AVN1 (S1, left) and the AVN2 (S2, right). Both strategies start with the drying of a lipid mixture of defined composition in a flask. Strategy S1 wraps Au NPs in liposomes formed in situ, whereas in S2 a lipid layer is assembled around octadecanethiol coated Au NPs.

DETAILED DESCRIPTION

Figure 1A:
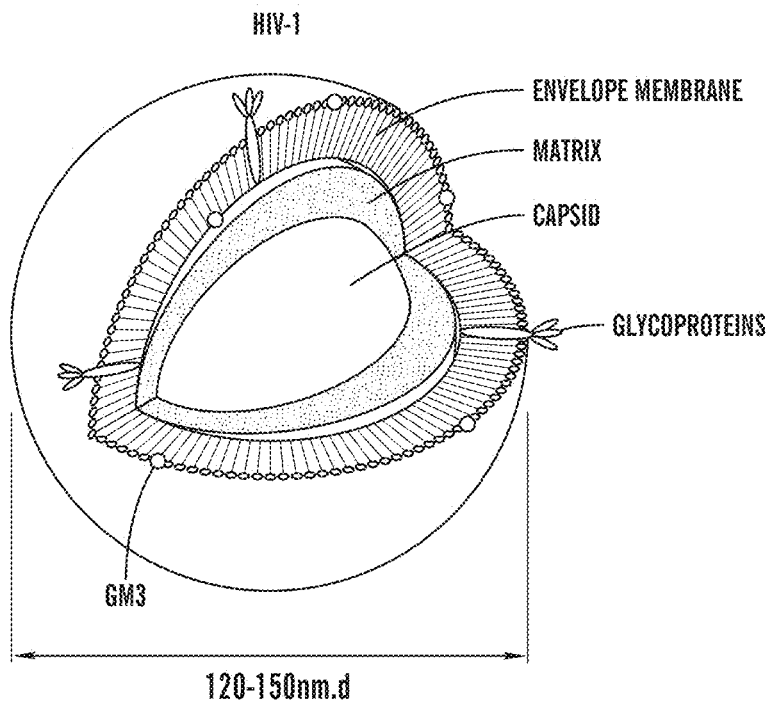
FIGS. 1a and 1b show the design of two embodiments of the claimed nanoparticles (NPs). The embodiments of NPs are named AVNs.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise defined herein, scientific and technical terms used in connection with the present application shall have the meanings that are commonly understood by those of ordinary skill in the art to which this disclosure belongs. It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

The present disclosure relates to ganglioside GM3-containing mixed lipids nanoparticles having an overall size between 60-100 nm, compositions comprising these GM3-containing mixed lipids nanoparticles, methods of making of these of ganglioside GM3-mixed lipids nanoparticles, and compositions comprising these nanoparticles. The ganglioside GM3-mixed lipids nanoparticles selectively targeted to CD169+ expressing cells such as dendritic cells and macrophages. The nanoparticles are subsequently endocytosed by the CD169+ expressing cells. The nanoparticles can facilitate in vivo studies of cellular processes in CD169+ expressing cells. The nanoparticles can facilitate target delivery of agents to CD169+ expressing cells.

It is known that the HIV attaches to and is internalized into mature dendritic cells via ganglioside-CD169 interactions. The ganglioside GM3 (aNeu5Ac(2-3)bDGalp(1-4)bDGlcp(1-1)Cer) is from the virus membrane and the CD169 is on the exterior of the mature dendritic cells. Artificial viral nanoparticles that mimic this unique GM3-CD169 interaction allow the study of the intercellular processes in mature dendritic cells after the internalization of viral particle that are entirely free of viral envelope glycoproteins or other potential interfering viral proteins, such as host-derived glycolipids or glycoproteins.

The inventors have made artificial viral nanoparticles composed of an inner solid core of gold core that is coated with a ganglioside GM3-containing mixed lipid composition layer. The ganglioside GM3-containing mixed lipid layer can be a bilayer or a monolayer where the mixed lipid is anchored to the core nanoparticle by an octodecanethiol layer. The ganglioside GM3-containing mixed lipid composition consisting of dipalmitoylphosphatidylcholine (DPPC), cholesterol, phosphatidylserine (PS), and GM3. In their experiments, the inventors used galactosylceramide (Gal-Cer) as a control to show that the sialic acid in GM3 is responsible for the observed binding.

The inventors found that the multivalent presentation of GM3 in a nanoparticle core platform facilitates the GM3 to retain a high degree of lateral mobility in a membrane monolayer or bilayer, thereby maximizes binding affinity of the GM3 ligands to their target CD169. The GM3-functionalized nanoparticles combine passive and active targeting strategies that are missing non-nano-conjugated GM3 based strategies. The tethering of the GM3 in a membrane monolayer retains a high degree of mobility for the ligands, which results in higher avidity when compared with simple lipid wrapped nanoparticles.

The inventors also found that the ganglioside GM3-containing mixed lipids nanoparticles combine the biological functionality of a membrane with the unique optical properties of noble metal nanoparticle probes, making the nanoparticles useful materials not only for delivery but also for imaging purposes.

Accordingly, provided herein is a nanoparticle comprising a core having a largest diameter between 50-90 nm, a coating layer encasing the core; and a ganglioside GM3-containing mixed lipid layer comprising of dipalmitoylphosphatidylcholine (DPPC), cholesterol, phosphatidylserine (PS), and aNeu5Ac(2-3)bDGalp(1-4)bDGlcp(1-1)Cer (GM3), wherein the ganglioside GM3-mixed lipid layer is exterior of the coating layer and is integrated into the coating layer, and wherein the nanoparticles have an overall particle size between 60-100 nm. In one embodiment, the ganglioside GM3-containing mixed lipid layer optionally comprises galactosylceramide (Gal-Cer).

As used herein, the phrase "integrated into the coating layer" means the hydrophobic interactions between the aliphatic coating on the nanoparticles and the hydrophobic tail of the lipid.

In the embodiment tested by the inventors, AVN1 and AVN2, the presentation of GM3 (or other ligands) in a membrane wrapped around a metal nanoparticle core is a unique approach that offers a series of novel functionalities: (1) The solid core stabilizes the membrane and facilitates the synthesis of membrane systems with much higher fluidity than is possible in conventional liposomes. The increase in fluidity makes it possible for multiple GM3 molecules to synergistically interact with receptors on the target cell, thereby maximization of avidity. (2) The solid core makes it possible to present GM3 on nanoparticles with diameters as small as 40 nm. The small particle size results in a minimization of phagocytosis through circulating macrophages and simultaneously ensures efficient binding to CD169 expressing macrophages, thus achieving maximization of targeting efficiency.

The hybrid nanoparticle combines the superb optical properties of the metal core with the biological functionality of a membrane. On way of looking at the lipid hybrid nanoparticle is that the core functions as a scaffold for the mixed lipid membrane. Additionally, the core can be used as scaffold for drugs and therapeutics.

In one embodiment of any nanoparticle described, the core is a solid core.

In another embodiment of any nanoparticle described, the core is a hollow core. In some embodiments, the core carries or contains therein agents, drugs or therapeutics.

The term "agent" refers to any entity which is normally not present or not present at the levels being administered to a cell, tissue or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

In another embodiment of any nanoparticle described, the core has perforations in its walls. The perforations are designed for time release of the agent(s) in the core. For example, in sustained drug delivery and selective delivery to the targeted CD 169+ expressing cells.

In one embodiment of any nanoparticle described, the core is has a shape that is selected from the group consisting of ellipsoid, spherical, rod-like, octahedral, and cube-like.

In one embodiment of any nanoparticle described, the core comprises a material that is a noble metal.

In another embodiment of any nanoparticle described, the core comprises a non-metal material.

In another embodiment of any nanoparticle described, the core comprises a mixture of a metal material and a non-metal material. In one embodiment, the metal material in the mixture is a noble metal.

In one embodiment of any nanoparticle described, the core comprises a material selected from the group consisting of gold, silver, a gold alloy, a silver alloy, silica, mesoporous silica, polystyrene, and titania. Non-limiting examples of alloy of gold are colored gold (silver, copper), crown gold (silver, copper), electrum (silver, copper), rhodite (rhodium), rose gold (copper), tumbaga (copper), and white gold (nickel, palladium). Non-limiting examples of alloy of silver are argentium sterling silver (copper, germanium), Billon, Britannia silver (copper), Dore bullion (gold), Electrum (gold), Goloid (copper, gold), Platinum sterling (platinum), shibuichi (copper), sterling silver (copper), and Tibetan silver (copper).

In another embodiment of any nanoparticle described, the core comprises a biodegradable material. For examples, biodegradable plastics such as polyhydroxyalkanoates, polylactic acid (PLA), polybutylene succinate (PBS), polycaprolactone (PCL), polyanhydrides, polyvinyl alcohol, and cellulose esters.

In one embodiment of any nanoparticle described, the coating layer functions to anchor the ganglioside GM3-containing mixed lipids to the core nanoparticle. In one embodiment, the coating layer tethers the ganglioside GM3-containing mixed lipid membrane monolayer on the core nanoparticle.

In one embodiment of any nanoparticle described, the coating layer is a thiolated lipid.

In one embodiment of any nanoparticle described, the coating layer or thiolated lipid comprises long-chain alkanes that terminate in a thiol. For example, octadecanethiol.

In one embodiment of any nanoparticle described, the long-chain alkane is a linear alkane having the general formula $CnH2n+2$ where $n \geq 5$.

In one embodiment of any nanoparticle described, the thiolated lipid is selected from the group consisting of octodecanethiol, hexadecane thiol, and heptadecane thiol.

In one embodiment of any nanoparticle described, the coating layer is a silane with long alkyl chains. For example, trimethoxy(octadecyl)silane. In one embodiment of any nanoparticle described, number of $—CH_2—$ group in the long the alkyl chains is greater or equal to five.

In one embodiment of any nanoparticle described, the silane is octadecylsilane.

In one embodiment of any nanoparticle described, the coating layer is polyethylene glycol thiol.

In one embodiment of any one of the nanoparticle described, the ganglioside GM3 containing mixed lipid layer consists of 40%-60% of DPPC, 1,2-dimyristoyl-sn-glycero-3-phosphocholine (DMPC) or 1,2-Distearoyl-sn-glycero-3-phosphocholine (DSPC).

In one embodiment of any one of the nanoparticle described, the ganglioside GM3 containing mixed lipid layer consists of a combination of two or more lipids selected from the group consisting of DPPC, DMPC and DSPC, wherein the combination of lipids make up ~40%-60% of the GM3 containing mixed lipid layer. For example, DPPC and DMPC mixture, DMPC and DSPC mixture, DPPC and DSPC mixture, and DPPC, DMPC and DSPC mixture.

In one embodiment of any nanoparticle described, the ganglioside GM3 containing mixed lipid layer consists of DPPC, cholesterol, PS, and GM3. In another embodiment, the ganglioside GM3 containing mixed lipid layer optionally contains Gal-Cer.

In one embodiment of any nanoparticle described, the ganglioside GM3 containing mixed lipid layer consists essentially of DPPC, cholesterol, PS, GM3, and Gal-Cer.

In one embodiment of any one of the nanoparticle described, the ganglioside GM3 containing mixed lipid layer comprises of DPPC, cholesterol, PS, and GM3 in one embodiment of any one of the nanoparticle described, the ganglioside GM3 containing mixed lipid layer consists of DPPC, cholesterol, PS, and GM3.

In one embodiment of any one of the nanoparticle described, the ganglioside GM3 containing mixed lipid layer consists essentially of DPPC, cholesterol, PS, and GM3.

In one embodiment of any one of the nanoparticle described, the ganglioside GM3 containing mixed lipid layer comprises of DPPC, cholesterol, PS, GM3 and Gal-Cer.

In one embodiment of any one of the nanoparticle described, the ganglioside GM3 containing mixed lipid layer consists of DPPC, cholesterol, PS, GM3 and Gal-Cer.

In one embodiment of any one of the nanoparticle described, the ganglioside GM3 containing mixed lipid layer consists essentially of DPPC, cholesterol, PS, GM3 and Gal-Cer.

In one embodiment of any one of the nanoparticle described, the ganglioside GM3 containing mixed lipid layer comprises of DMPC, cholesterol, PS, and GM3.

In one embodiment of any one of the nanoparticle described, the ganglioside GM3 containing mixed lipid layer consists of DMPC, cholesterol, PS, and GM3.

In one embodiment of any one of the nanoparticle described, the ganglioside GM3 containing mixed lipid layer consists essentially of DMPC, cholesterol, PS, and GM3.

In one embodiment of any one of the nanoparticle described, the ganglioside GM3 containing mixed lipid layer comprises of DMPC, cholesterol, PS, GM3 and Gal-Cer.

In one embodiment of any one of the nanoparticle described, the ganglioside GM3 containing mixed lipid layer consists of DMPC, cholesterol, PS, GM3 and Gal-Cer.

In one embodiment of any one of the nanoparticle described, the ganglioside GM3 containing mixed lipid layer consists essentially of DMPC, cholesterol, PS, GM3 and Gal-Cer.

In one embodiment of any one of the nanoparticle described, the ganglioside GM3 containing mixed lipid layer comprises of DSPC, cholesterol, PS, and GM3.

In one embodiment of any one of the nanoparticle described, the ganglioside GM3 containing mixed lipid layer consists of DSPC, cholesterol, PS, and GM3.

In one embodiment of any one of the nanoparticle described, the ganglioside GM3 containing mixed lipid layer consists essentially of DSPC, cholesterol, PS, and GM3.

In one embodiment of any one of the nanoparticle described, the ganglioside GM3 containing mixed lipid layer comprises of DSPC, cholesterol, PS, GM3 and Gal-Cer.

In one embodiment of any one of the nanoparticle described, the ganglioside GM3 containing mixed lipid layer consists of DSPC, cholesterol, PS, GM3 and Gal-Cer.

In one embodiment of any one of the nanoparticle described, the ganglioside GM3 containing mixed lipid layer consists essentially of DSPC, cholesterol, PS, GM3 and Gal-Cer.

In one embodiment of any one of the nanoparticle described, the ganglioside GM3 containing mixed lipid layer comprises of a combination of two or more lipids selected from the group consisting of DPPC, DMPC and DSPC, and cholesterol, PS, and GM3.

In one embodiment of any one of the nanoparticle described, the ganglioside GM3 containing mixed lipid layer consists of a combination of two or more lipids selected from the group consisting of DPPC, DMPC and DSPC, and cholesterol, PS, and GM3.

In one embodiment of any one of the nanoparticle described, the ganglioside GM3 containing mixed lipid layer consists essentially of a combination of two or more lipids selected from the group consisting of DPPC, DMPC and DSPC, and cholesterol, PS, and GM3.

In one embodiment of any one of the nanoparticle described, the ganglioside GM3 containing mixed lipid layer comprises of a combination of two or more lipids selected from the group consisting of DPPC, DMPC and DSPC, and cholesterol, PS, GM3 and Gal-Cer.

In one embodiment of any one of the nanoparticle described, the ganglioside GM3 containing mixed lipid layer consists of a combination of two or more lipids selected from the group consisting of DPPC, DMPC and DSPC, and cholesterol, PS, GM3 and Gal-Cer.

In one embodiment of any one of the nanoparticle described, the ganglioside GM3 containing mixed lipid layer consists essentially of a combination of two or more lipids selected from the group consisting of DPPC, DMPC and DSPC, and cholesterol, PS, GM3 and Gal-Cer.

In one embodiment of any nanoparticle described, the nanoparticle comprises a second layer of ganglioside GM3 containing mixed lipid.

In one embodiment of any nanoparticle described, the ganglioside GM3 containing mixed lipid layer forms a lipid bilayer.

In one embodiment of any nanoparticle described, the ganglioside GM3 containing mixed lipid layer forms a lipid monolayer.

In one embodiment of any nanoparticle described, the DPPC, DMPC or DSPC in the ganglioside GM3 containing mixed lipid layer consists of 40%-60% of DPPC, DMPC or DSPC respectively. In other embodiments, the DPPC, DMPC or DSPC in the mixed lipid layer is about 41%, 42%, 43%, 44%, 45%, 46%, 47%, 48%, 49%, 50%, 51%, 52%, 53%, 54%, 55%, 56%, 57%, 58%, or 59%. In one embodiment of any nanoparticle described, the ganglioside GM3 containing mixed lipid layer consists of 51% of DPPC, DMPC or DSPC.

In one embodiment of any nanoparticle described, the combination or mixture of two or more lipids selected from the group consisting of DPPC, DMPC and DSPC make up 40%-60% of the ganglioside GM3 containing mixed lipid layer. In another embodiment of any nanoparticle described, the combination or mixture of two or more lipids selected from the group consisting of DPPC, DMPC and DSPC make up about 41%, 42%, 43%, 44%, 45%, 46%, 47%, 48%, 49%, 50%, 51%, 52%, 53%, 54%, 55%, 56%, 57%, 58%, or 59% of the ganglioside GM3 containing mixed lipid layer. In one embodiment of any nanoparticle described, the combination or mixture of two or more lipids selected from the group consisting of DPPC, DMPC and DSPC make up 51% of the ganglioside GM3 containing mixed lipid layer.

In one embodiment of any nanoparticle described, the cholesterol in the ganglioside GM3 containing mixed lipid layer consists of 40%-60% of cholesterol. In one embodiment of any nanoparticle described, the ganglioside GM3 containing mixed lipid layer consists of 45% of cholesterol. In other embodiments, the cholesterol in the mixed lipid layer is about 41%, 42%, 43%, 44%, 45%, 46%, 47%, 48%, 49%, 50%, 51%, 52%, 53%, 54%, 55%, 56%, 57%, 58%, or 59%.

In one embodiment of any nanoparticle described, the PS in the ganglioside GM3 containing mixed lipid layer consists of 0.5%-5% of PS. In one embodiment of any nanoparticle described, the PS in the ganglioside GM3 containing mixed lipid layer consists of 1% of PS. In other embodiments, the PS in the mixed lipid layer is about 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or 5.0%.

In one embodiment of any nanoparticle described, the GM3 in the ganglioside GM3 containing mixed lipid layer consists of 0.1%-6% of GM3.

In another embodiment of any nanoparticle described, the GM3 in the ganglioside GM3 containing mixed lipid layer consists of 0.1%-3% of GM3.

In one embodiment of any nanoparticle described, the GM3 in the ganglioside GM3 containing mixed lipid layer consists of 3% of GM3.

In other embodiments, the GM3 in the mixed lipid layer is about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0%.

In one embodiment of any nanoparticle described, the Gal-Cer in the ganglioside GM3 containing mixed lipid layer consists of 0.1%-6% of Gal-Cer.

In one embodiment of any nanoparticle described, the Gal-Cer in the ganglioside GM3 containing mixed lipid layer consists of 0.1%-3% of Gal-Cer.

In one embodiment of any nanoparticle described, the Gal-Cer in the ganglioside GM3 containing mixed lipid layer consists of 1% of Gal-Cer.

In other embodiments, the Gal-Cer in the mixed lipid layer is about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0%.

In one embodiment of any nanoparticle described, the ganglioside GM3 containing mixed lipid comprises 51-53% DPPC, 45% cholesterol, 1% PS, and 1-3% GM3.

In one embodiment of any nanoparticle described, the ganglioside GM3 containing mixed lipid comprises 51% DPPC, 45% cholesterol, 1% PS, and 3% GM3.

In one embodiment of any nanoparticle described, the ganglioside GM3 containing mixed lipid comprises 52% DPPC, 45% cholesterol, 1% PS, and 2% GM3.

In one embodiment of any nanoparticle described, the ganglioside GM3 containing mixed lipid comprises 53% DPPC, 45% cholesterol, 1% PS, and 1% GM3.

In one embodiment of any nanoparticle described, the ganglioside GM3 containing mixed lipid comprises 51-53% DMPC, 45% cholesterol, 1% PS, and 1-3% GM3.

In one embodiment of any nanoparticle described, the ganglioside GM3 containing mixed lipid comprises 51% DMPC, 45% cholesterol, 1% PS, and 3% GM3.

In one embodiment of any nanoparticle described, the ganglioside GM3 containing mixed lipid comprises 52% DMPC, 45% cholesterol, 1% PS, and 2% GM3.

In one embodiment of any nanoparticle described, the ganglioside GM3 containing mixed lipid comprises 53% DMPC, 45% cholesterol, 1% PS, and 1% GM3.

In one embodiment of any nanoparticle described, the ganglioside GM3 containing mixed lipid comprises 51-53% DSPC, 45% cholesterol, 1% PS, and 1-3% GM3.

In one embodiment of any nanoparticle described, the ganglioside GM3 containing mixed lipid comprises 51% DSPC, 45% cholesterol, 1% PS, and 3% GM3.

In one embodiment of any nanoparticle described, the ganglioside GM3 containing mixed lipid comprises 52% DSPC, 45% cholesterol, 1% PS, and 2% GM3.

In one embodiment of any nanoparticle described, the ganglioside GM3 containing mixed lipid comprises 53% DSPC, 45% cholesterol, 1% PS, and 1% GM3.

In one embodiment of any nanoparticle described, the ganglioside GM3 containing mixed lipid comprises 51-53% of a combination or mixture of lipids selected from the group consisting of DPPC, DMPC and DSPC, 45% cholesterol, 1% PS, and 1-3% GM3, wherein the combination or mixture of lipids make up 51-53% of ganglioside GM3 containing mixed lipid layer.

In one embodiment of any nanoparticle described, the ganglioside GM3 containing mixed lipid comprises 51% of a combination or mixture of lipids selected from the group consisting of DPPC, DMPC and DSPC, 45% cholesterol, 1% PS, and 3% GM3, wherein the combination or mixture of lipids make up 51% of ganglioside GM3 containing mixed lipid layer.

In one embodiment of any nanoparticle described, the ganglioside GM3 containing mixed lipid comprises 52% of a combination or mixture of lipids selected from the group consisting of DPPC, DMPC and DSPC, 45% cholesterol, 1% PS, and 2% GM3, wherein the combination or mixture of lipids make up 52% of ganglioside GM3 containing mixed lipid layer.

In one embodiment of any nanoparticle described, the ganglioside GM3 containing mixed lipid comprises 53% of a combination or mixture of two or more lipids selected from the group consisting of DPPC, DMPC and DSPC, 45% cholesterol, 1% PS, and 1% GM3, wherein the combination or mixture of lipids make up 51% of ganglioside GM3 containing mixed lipid layer.

In some embodiments of any nanoparticle described, the combination or mixture of two or more lipids selected from the group consisting of DPPC, DMPC and DSPC can be in the ratio of 1:1:1, 3:1:1, 5:1:1, 4:1:1, 3:2:1, or 2:1:1.

In one embodiment of any nanoparticle described, the ganglioside GM3 containing mixed lipid comprises ~51-52% DPPC, 45% cholesterol, 1% PS, ~1-3% GM3 and ~1-3% Gal-Cer.

In one embodiment of any nanoparticle described, the ganglioside GM3 containing mixed lipid layer forms a lipid bilayer and comprises ~51-53% DPPC, 45% cholesterol, 1% PS, and ~1-3% GM3.

In one embodiment of any nanoparticle described, the ganglioside GM3 containing mixed lipid layer forms a lipid bilayer and comprises 51% DSPC, 45% cholesterol, 1% PS, and 3% GM3.

In one embodiment of any nanoparticle described, the ganglioside GM3 containing mixed lipid layer forms a lipid bilayer and comprises 52% DSPC, 45% cholesterol, 1% PS, and 2% GM3.

In one embodiment of any nanoparticle described, the ganglioside GM3 containing mixed lipid layer forms a lipid bilayer and comprises 53% DSPC, 45% cholesterol, 1% PS, and 1% GM3.

In one embodiment of any nanoparticle described, the ganglioside GM3 containing mixed lipid layer forms a lipid bilayer and comprises 51% of a combination or mixture of lipids selected from the group consisting of DPPC, DMPC and DSPC, 45% cholesterol, 1% PS, and 3% GM3, wherein the combination or mixture of lipids make up 51% of ganglioside GM3 containing mixed lipid layer.

In one embodiment of any nanoparticle described, the ganglioside GM3 containing mixed lipid layer forms a lipid bilayer and comprises 52% of a combination or mixture of lipids selected from the group consisting of DPPC, DMPC and DSPC, 45% cholesterol, 1% PS, and 2% GM3, wherein the combination or mixture of lipids make up 52% of ganglioside GM3 containing mixed lipid layer.

In one embodiment of any nanoparticle described, the ganglioside GM3 containing mixed lipid layer forms a lipid bilayer and comprises 53% of a combination or mixture of lipids selected from the group consisting of DPPC, DMPC and DSPC, 45% cholesterol, 1% PS, and 1% GM3, wherein the combination or mixture of lipids make up 52% of ganglioside GM3 containing mixed lipid layer.

In one embodiment of any nanoparticle described, the ganglioside GM3 containing mixed lipid layer forms a lipid bilayer and comprises ~51-52% DPPC, 45% cholesterol, 1% PS, ~1-3% GM3 and ~1-3% Gal-Cer.

In one embodiment of any nanoparticle described, the ganglioside GM3 containing mixed lipid layer forms a lipid monolayer and comprises 51-53% DPPC, 45% cholesterol, 1% PS, and 1-3% GM3.

In one embodiment of any nanoparticle described, the ganglioside GM3 containing mixed lipid layer forms a lipid monolayer and comprises 51% DSPC, 45% cholesterol, 1% PS, and 3% GM3.

In one embodiment of any nanoparticle described, the ganglioside GM3 containing mixed lipid layer forms a lipid monolayer and comprises 52% DSPC, 45% cholesterol, 1% PS, and 2% GM3.

In one embodiment of any nanoparticle described, the ganglioside GM3 containing mixed lipid layer forms a lipid monolayer and comprises 53% DSPC, 45% cholesterol, 1% PS, and 1% GM3.

In one embodiment of any nanoparticle described, the ganglioside GM3 containing mixed lipid layer forms a lipid monolayer and comprises 51% of a combination or mixture of lipids selected from the group consisting of DPPC, DMPC and DSPC, 45% cholesterol, 1% PS, and 3% GM3, wherein the combination or mixture of lipids make up 51% of ganglioside GM3 containing mixed lipid layer.

In one embodiment of any nanoparticle described, the ganglioside GM3 containing mixed lipid layer forms a lipid monolayer and comprises 52% of a combination or mixture of lipids selected from the group consisting of DPPC, DMPC and DSPC, 45% cholesterol, 1% PS, and 2% GM3, wherein the combination or mixture of lipids make up 52% of ganglioside GM3 containing mixed lipid layer.

In one embodiment of any nanoparticle described, the ganglioside GM3 containing mixed lipid layer forms a lipid monolayer and comprises 53% of a combination or mixture of lipids selected from the group consisting of DPPC, DMPC and DSPC, 45% cholesterol, 1% PS, and 1% GM3, wherein the combination or mixture of lipids make up 52% of ganglioside GM3 containing mixed lipid layer.

In one embodiment of any nanoparticle described, the ganglioside GM3 containing mixed lipid layer forms a lipid monolayer and comprises 51% DPPC, 45% cholesterol, 1% PS, 3% GM3 and 3% Gal-Cer.

In one embodiment of any nanoparticle described, the lipid further comprises a labeling agent. For example, a fluorescent dye for imaging, tracking and detection. Non-limiting examples include lipophilic fluorescent dyes such as DiI, DiO, DiD, DiA, and DiR (INVITROGEN™).

The inventors have developed a new class of theranostic nanoparticles that contain the monosialodiglycosylganglioside GM3 embedded into a membrane wrapped around a metal (e.g., gold) core nanoparticle. The GM3 functionalized nanoparticles recognize the Siglec1, CD169, which is selectively expressed on myeloid dendritic cells and in inflammatory monocytes and macrophage subsets that play a key pathogenic role in many diseases, including but not restricted to autoimmune diseases such as arthritis, lupus and scleroderma; nephrotoxic nephritis; CNS inflammatory disorders, such as EAE.

Alternatively, CD169+ macrophages play a critical role in development of adaptive immune responses to tumor antigens and promote tumoricidal response. Thus selective targeting of this immunologically active macrophage subset using the embodied GM3-displaying gold nanoparticles will provide unique therapeutic insights into both inflammatory and immunoregulatory settings.

Accordingly, in some embodiments, the ganglioside GM3-mixed lipid layer nanoparticles comprise agents, drugs or therapeutics that modulate the inflammatory response of the CD169+ macrophages. For example, the ganglioside GM3-mixed lipid layer nanoparticles carry and selectively deliver agents that suppress the inflammatory response of the CD169+ macrophages, thereby reducing the inflammatory response to "self" molecules in a subject. Such nanoparticles would be useful in the treatment and/or prevention and/or management of autoimmune diseases. GM3-mixed lipid layer nanoparticles will incorporate immune-suppression agents such as those targeting signal transduction pathways responsible for pro-inflammatory cytokine production to selectively inhibit an over-exuberant immune response in inflammatory myeloid cells. These include, but not limited to inhibitors of tyrosine phosphatases, tyrosine kinases and NF-κB dependent signal transduction.

In other embodiments, the ganglioside GM3-mixed lipid layer nanoparticles carry and selectively deliver agents that enhance or stimulate the inflammatory response of the CD169+ macrophages, thereby promoting the inflammatory response in a subject. Such nanoparticles would be useful in the treatment and/or management of cancers, tumors and pathogenic infections. GM3-mixed lipid layer nanoparticles will incorporate anti-PD-L1 antibodies to block PD-L1 interactions with PD-1 receptor on T cells (to block immune-inhibitory receptors). For example, such selective targeting of anti-PD-L1 antibodies to CD169+ myeloid DCs and macrophages will be achieved with GM3-nanoparticles to reactivate host immune response as a novel strategy of cancer immunotherapy.

In one embodiment, provided herein is a method of making a nanoparticle containing ganglioside GM3-mixed lipid layer described comprising the step of (a) contacting a core nanoparticle with a coating layer material to coat the particle; (b) adding the coated core nanoparticle to a ganglioside GM3 containing mixed lipid solution; (c) sonicating the contacted mixture of step (b) for a period of time; (d) extruding the particles from step (c) through a membrane with a pore size of about 100-200 nm; and (e) collecting the extruded nanoparticles from the membrane.

In one embodiment, provided herein is a method of making a nanoparticle containing ganglioside GM3-mixed lipid layer described herein comprising (a) adding a thiolated lipid to a core nanoparticle to coat the particle; (b) sonicating a ganglioside GM3 containing mixed lipid solution for a period of time to form liposomes; (c) adding the thiolaled lipid coated particle of step (a) to the liposomes of step (b); and (d) collecting nanoparticles formed.

In one embodiment, the nanoparticle containing ganglioside GM3-mixed lipid layer described is made according to the following method. 1 mL of $1.1 \times 10^{10}$ particles/ml colloidal gold nanoparticles (Au NPs) with a nominal diameter of 80 nm (Ted Pella) were incubated with 5 µl 10 mM polyethylene glycol thiol propionic acid overnight, followed by 3 cycles of washing through centrifugation (2500 rpm 10 min) and resuspension in double distilled water (ddi water) to remove excess acid-PEG. The functionalized Au nanoparticles (Au NPs) were resuspended into 1 ml 10 mM NaCl, pH=7. Simultaneously, a total amount of 1 µmole of lipid mixture (Avanti Polar Lipids, Alabaster, Ala.) was dissolved in 100 µl chloroform in a clean 25 mL round-bottom flask. The lipid mixture comprises 51% DPPC, 45% cholesterol, 1% PS, and 3% GM3. The lipid mixture was then sonicated for 5 s, followed by rotary evaporation for 15 min. A uniformly thin lipid dry layer formed on the bottom of the flask, which was further dried under vacuum overnight. The above acid-PEG functionalized Au NPs solution was injected into the flask through a disposable syringe to rehydrate the lipid film in the presence of Au NPs at 50° C. for 1 h. Subsequently, 30 min sonication was applied to agitate the suspension and maximize lipid hydration. Immediately after sonication, the lipid-Au NP mixture was transferred into a cryo-vial under Ar protection, and underwent 3 freeze-thaw cycles in liquid nitrogen and 50° C. water. After another sonication step of 30 min, the solution was extruded through a 200 nm-pore-size polystyrene membrane with a mini-extruder set (Avanti Polar Lipids). AVNs were then purified from free liposomes through 3 cycles of centrifugation (2500 rpm, 10 min), and resuspended in 100 µl 10 mM NaCl for further use.

In another embodiment, the nanoparticle containing ganglioside GM3-mixed lipid layer described is made according to the following method. A thin dry layer of lipid mixture was prepared following the procedures described supra. 1 ml of 20 mM HEPES buffer (pH=7.2) was then added, forming a cloudy solution after vigorous agitation. The mixture was then sonicated for 30 min in ice bath until the solution became clear. This liposome solution was then stored in 4° C. for further use. 1 ml 100 nm colloidal Au NP solution ($1.1 \times 10^{10}$ particles/ml) was pelleted via centrifugation at 2500 rpm for 10 min. 0.5 ml of the prepared liposome solution was added to the Au pellet, and the volume was increased to 1 ml with 20 mM HEPES buffer. 200 µl of 0.01 mg ml-1 1-octedecane-thiol solution in ethanol was then added dropwise to the mixture. The mixed solution was agitated overnight on a rotator. After that, the AVNs were washed three times through centrifugation (2500 rpm, 10 min) and resuspension in ddi water. Finally, the AVN pellet was resuspended in 100 µl 20 mM HEPES buffer and ready to use.

In one embodiment, provided herein is a composition comprising a nanoparticle described herein in a physiologically acceptable carrier. The term "carrier" refers to a diluent, adjuvant, excipient, or vehicle with which the composition is administered. Such physiologically acceptable carriers can be sterile liquids, such as water and oils, including those of petroleum, animal, vegetable or synthetic origin, such as peanut oil, soybean oil, mineral oil, sesame oil and the like. Water is a preferred carrier when the composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

In one embodiment, physiologically acceptable means "pharmaceutically acceptable."

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In one embodiment, provided herein is a composition comprising nanoparticles containing ganglioside GM3-mixed lipid described herein this disclosure.

In one embodiment, provided herein is a composition comprising nanoparticles containing ganglioside GM3-mixed lipid, wherein the mixed lipid composition coated nanoparticle comprises GM3, cholesterol, PS, and at least one lipid selected from the group consisting DPPC, DMPC and DSPC. The nanoparticles of the compositions can optionally contain Gal-Cer.

In one embodiment, provided herein is a method of delivering a nanoparticle into a cell comprising adding a nanoparticle described herein to a CD169-expressing eukaryotic cell under conditions that permit the nanoparticle to be endocytosed into the CD169-expressing eukaryotic cell, and waiting for a sufficient time for endocytosis to occur.

In one embodiment of any method described, the CD169-expressing eukaryotic cell is a Hela cell, a dendritic cell or a macrophage.

In one embodiment of any method described, the conditions that permit the nanoparticle to be endocytosed means physiological conditions for the CD169-expressing eukaryotic cell. For example, under normal tissue culture conditions.

In one embodiment of any method described, the nanoparticle is sequestered within non-lysosomal tetraspanin-positive compartments of the CD169-expressing eukaryotic cell.

In one embodiment, provided herein is a method of studying the interaction between CD169+ dendritic cells or macrophage and CD4+ T cells comprising: contacting a CD169+ dendritic cell or macrophage with a ganglioside GM3-mixed lipid nanoparticle described herein; allowing the nanoparticle to be taken up into the CD169+ dendritic cell or macrophage; contacting the cell of step b with a CD4+ T cells; and observing the interaction between the CD169+ dendritic cell or macrophage and the CD4+ T cell.

In one embodiment of any method described, the core is a solid core.

In one embodiment of any method described, the core is has a shape that is selected from the group consisting of ellipsoid, spherical, rod-like, octahedral, and cube-like.

In one embodiment of any method described, the core comprises a material that is a noble metal.

In another embodiment of any method described, the core comprises a non-metal material.

In another embodiment of any method described, the core comprises a mixture of a metal material and a non-metal material. In one embodiment, the metal material in the mixture is a noble metal.

In one embodiment of any method described, the core comprises a material selected from the group consisting of gold, silver, a gold alloy, a silver alloy, silica, mesoporous silica, polystyrene, and titania. Non-limiting examples of alloy of gold are colored gold (silver, copper), crown gold (silver, copper), electrum (silver, copper), rhodite (rhodium), rose gold (copper), tumbaga (copper), and white gold (nickel, palladium). Non-limiting examples of alloy of silver are argentium sterling silver (copper, germanium), Billon, Britannia silver (copper), Dore bullion (gold), Electrum (gold), Goloid (copper, gold), Platinum sterling (platinum), shibuichi (copper), sterling silver (copper), and Tibetan silver (copper).

In one embodiment of any method described, the coating layer functions to anchor the ganglioside GM3-containing mixed lipids to the core.

In one embodiment of any method described, the coating layer is a thiolated lipid.

In one embodiment of any method described, the coating layer or thiolated lipid comprises long-chain alkanes that terminate in a thiol.

In one embodiment of any method described, the long-chain alkane is a linear alkane having the general formula $C_nH_{2n+2}$ where $n \geq 5$.

In one embodiment of any method described, the thiolated lipid is selected from the group consisting of octodecanethiol, hexadecane thiol, and heptadecane thiol.

In one embodiment of any method described, the coating layer is a silane with long alkyl chains. In one embodiment of any nanoparticle described, number of —$CH_2$— group in the long the alkyl chains is greater or equal to five.

In one embodiment of any method described, the silane is octadecylsilane.

In one embodiment of any method described, the coating layer is polyethylene glycol thiol.

In one embodiment of any method described, the ganglioside GM3 containing mixed lipid layer of the described nanoparticles consists of cholesterol, PS, GM3, and at least one lipid selected from the group consisting of DPPC, DMPC and DSPC. The ganglioside GM3 containing mixed lipid layer of the described nanoparticles may consists of a combination or a mixture of two or more lipids selected from the group consisting of DPPC, DMPC and DSPC. For example, DPPC and DMPC, DPPC and DSPC, DMPC and DSPC, and DPPC, DMPC and DSPC. The nanoparticle can optionally contain Gal-Cer.

In one embodiment of any method described, the ganglioside GM3 containing mixed lipid layer of the described nanoparticles consists of DPPC, cholesterol, PS, and GM3.

In one embodiment of any method described, the ganglioside GM3 containing mixed lipid layer of the described nanoparticles consists of DMPC, cholesterol, PS, and GM3.

In one embodiment of any method described, the ganglioside GM3 containing mixed lipid layer of the described nanoparticles consists of DSPC, cholesterol, PS, and GM3.

In one embodiment of any method described, the ganglioside GM3 containing mixed lipid layer of the described nanoparticles consists essentially of cholesterol, PS, GM3, and at least one lipid selected from the group consisting of DPPC, DMPC and DSPC.

In one embodiment of any method described, the ganglioside GM3 containing mixed lipid layer of the described nanoparticles consists essentially of DPPC, cholesterol, PS, and GM3.

In one embodiment of any method described, the ganglioside GM3 containing mixed lipid layer of the described nanoparticles consists essentially of DMPC, cholesterol, PS, and GM3.

In one embodiment of any method described, the ganglioside GM3 containing mixed lipid layer of the described nanoparticles consists essentially of DSPC, cholesterol, PS, and GM3.

In one embodiment of any method described, the ganglioside GM3 containing mixed lipid layer of the described nanoparticles consists of cholesterol, PS, GM3, Gal-Cer, and at least one lipid selected from the group consisting of DPPC, DMPC and DSPC. The ganglioside GM3 containing mixed lipid layer of the described nanoparticles may consists of a combination or a mixture of two or more lipids selected from the group consisting of DPPC, DMPC and DSPC. For example, DPPC and DMPC, DPPC and DSPC, DMPC and DSPC, and DPPC, DMPC and DSPC.

In one embodiment of any method described, the ganglioside GM3 containing mixed lipid layer of the described nanoparticles consists of DPPC, cholesterol, PS, GM3, and Gal-Cer.

In one embodiment of any method described, the ganglioside GM3 containing mixed lipid layer of the described nanoparticles consists of DMPC, cholesterol, PS, GM3, and Gal-Cer.

In one embodiment of any method described, the ganglioside GM3 containing mixed lipid layer of the described nanoparticles consists of DSPC, cholesterol, PS, GM3, and Gal-Cer.

In one embodiment of any method described, the ganglioside GM3 containing mixed lipid layer consists essentially of DPPC, cholesterol, PS, GM3, and Gal-Cer.

In one embodiment of any method described, the ganglioside GM3 containing mixed lipid layer of the described nanoparticles consists essentially of DMPC, cholesterol, PS, GM3, and Gal-Cer.

In one embodiment of any method described, the ganglioside GM3 containing mixed lipid layer of the described nanoparticles consists essentially of DSPC, cholesterol, PS, GM3, and Gal-Cer.

In one embodiment of any method described, the nanoparticle comprises a second layer of ganglioside GM3 containing mixed lipid.

In one embodiment of any method described, the ganglioside GM3 containing mixed lipid layer forms a lipid bilayer.

In one embodiment of any method described, the ganglioside GM3 containing mixed lipid layer forms a lipid monolayer.

In one embodiment of any method described, the DPPC, DMPC or DSPC in the ganglioside GM3 containing mixed lipid layer consists of 40%-60% of DPPC, DMPC or DSPC respectively. In other embodiments, the DPPC, DMPC or DSPC in the mixed lipid layer is about 41%, 42%, 43%, 44%, 45%, 46%, 47%, 48%, 49%, 50%, 51%, 52%, 53%, 54%, 55%, 56%, 57%, 58%, or 59%. In one embodiment of any method described, the ganglioside GM3 containing mixed lipid layer consists of 51% of DPPC, DMPC or DSPC.

In one embodiment of any method described, the combination or mixture of two or more lipids selected from the group consisting of DPPC, DMPC and DSPC make up 40%-60% of the ganglioside GM3 containing mixed lipid layer. In another embodiment of any method described, the combination or mixture of two or more lipids selected from the group consisting of DPPC, DMPC and DSPC make up about 41%, 42%, 43%, 44%, 45%, 46%, 47%, 48%, 49%, 50%, 51%, 52%, 53%, 54%, 55%, 56%, 57%, 58%, or 59% of the ganglioside GM3 containing mixed lipid layer.

In one embodiment of any method described, the combination or mixture of two or more lipids selected from the group consisting of DPPC, DMPC and DSPC make up 51% of the ganglioside GM3 containing mixed lipid layer.

In one embodiment of any method described, the combination or mixture of two or more lipids selected from the group consisting of DPPC, DMPC and DSPC make up 52% of the ganglioside GM3 containing mixed lipid layer.

In one embodiment of any method described, the combination or mixture of two or more lipids selected from the group consisting of DPPC, DMPC and DSPC make up 53% of the ganglioside GM3 containing mixed lipid layer.

In one embodiment of any method described, the DPPC in the ganglioside GM3 containing mixed lipid layer consists of 40%-60% of DPPC. In other embodiments, the DPPC in the mixed lipid layer is about 41%, 42%, 43%, 44%, 45%, 46%, 47%, 48%, 49%, 50%, 51%, 52%, 53%, 54%, 55%, 56%, 57%, 58%, or 59%.

In one embodiment of any method described, the ganglioside GM3 containing mixed lipid layer consists of 51% of DPPC.

In one embodiment of any method described, the ganglioside GM3 containing mixed lipid layer consists of 52% of DPPC.

In one embodiment of any method described, the ganglioside GM3 containing mixed lipid layer consists of 53% of DPPC.

In one embodiment of any method described, the cholesterol in the ganglioside GM3 containing mixed lipid layer consists of 40%-60% of cholesterol. In one embodiment of any nanoparticle described, the ganglioside GM3 containing mixed lipid layer consists of 45% of cholesterol. In other embodiments, the cholesterol in the mixed lipid layer is about 41%, 42%, 43%, 44%, 45%, 46%, 47%, 48%, 49%, 50%, 51%, 52%, 53%, 54%, 55%, 56%, 57%, 58%, or 59%.

In one embodiment of any method described, the PS in the ganglioside GM3 containing mixed lipid layer consists of 0.5%-5% of PS. In one embodiment of any nanoparticle described, the PS in the ganglioside GM3 containing mixed lipid layer consists of 1% of PS. In other embodiments, the PS in the mixed lipid layer is about 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or 5.0%.

In one embodiment of any method described, the GM3 in the ganglioside GM3 containing mixed lipid layer consists of 0.1%-6% of GM3.

In one embodiment of any method described, the GM3 in the ganglioside GM3 containing mixed lipid layer consists of 0.1%-3% of GM3.

In one embodiment of any method described, the GM3 in the ganglioside GM3 containing mixed lipid layer consists of 3% of GM3.

In other embodiments, the GM3 in the mixed lipid layer is about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0%.

In one embodiment of any method described, the Gal-Cer in the ganglioside GM3 containing mixed lipid layer consists of 0.1%-6% of Gal-Cer.

In one embodiment of any method described, the Gal-Cer in the ganglioside GM3 containing mixed lipid layer consists of 0.1%-6% of Gal-Cer.

In one embodiment of any method described, the Gal-Cer in the ganglioside GM3 containing mixed lipid layer consists of 1% of Gal-Cer.

In other embodiments of any method described, the Gal-Cer in the mixed lipid layer is about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0%.

In one embodiment of any method described, the ganglioside GM3 containing mixed lipid comprises 51-53% DPPC, 45% cholesterol, 1% PS, and 1-3% GM3.

In one embodiment of any method described, the ganglioside GM3 containing mixed lipid comprises 51% DPPC, 45% cholesterol, 1% PS, and 3% GM3.

In one embodiment of any method described, the ganglioside GM3 containing mixed lipid comprises 52% DPPC, 45% cholesterol, 1% PS, and 2% GM3.

In one embodiment of any method described, the ganglioside GM3 containing mixed lipid comprises 53% DPPC, 45% cholesterol, 1% PS, and 1% GM3.

In one embodiment of any method described, the ganglioside GM3 containing mixed lipid comprises 51-53% DMPC, 45% cholesterol, 1% PS, and 1-3% GM3.

In one embodiment of any method described, the ganglioside GM3 containing mixed lipid comprises 51% DMPC, 45% cholesterol, 1% PS, and 3% GM3.

In one embodiment of any method described, the ganglioside GM3 containing mixed lipid comprises 52% DMPC, 45% cholesterol, 1% PS, and 2% GM3.

In one embodiment of any method described, the ganglioside GM3 containing mixed lipid comprises 53% DMPC, 45% cholesterol, 1% PS, and 1% GM3.

In one embodiment of any method described, the ganglioside GM3 containing mixed lipid comprises 51-53% DSPC, 45% cholesterol, 1% PS, and 1-3% GM3.

In one embodiment of any method described, the ganglioside GM3 containing mixed lipid comprises 51% DSPC, 45% cholesterol, 1% PS, and 3% GM3.

In one embodiment of any method described, the ganglioside GM3 containing mixed lipid comprises 52% DSPC, 45% cholesterol, 1% PS, and 2% GM3.

In one embodiment of any method described, the ganglioside GM3 containing mixed lipid comprises 53% DSPC, 45% cholesterol, 1% PS, and 1% GM3.

In one embodiment of any method described, the ganglioside GM3 containing mixed lipid comprises 51-53% of a combination or mixture of lipids selected from the group consisting of DPPC, DMPC and DSPC, 45% cholesterol, 1% PS, and 1-3% GM3, wherein the combination or mixture of lipids make up 51-53% of ganglioside GM3 containing mixed lipid layer.

In one embodiment of any method described, the ganglioside GM3 containing mixed lipid comprises 51% of a combination or mixture of lipids selected from the group consisting of DPPC, DMPC and DSPC, 45% cholesterol, 1% PS, and 3% GM3, wherein the combination or mixture of lipids make up 51% of ganglioside GM3 containing mixed lipid layer.

In one embodiment of any method described, the ganglioside GM3 containing mixed lipid comprises 52% of a combination or mixture of lipids selected from the group consisting of DPPC, DMPC and DSPC, 45% cholesterol, 1% PS, and 2% GM3, wherein the combination or mixture of lipids make up 52% of ganglioside GM3 containing mixed lipid layer.

In one embodiment of any method described, the ganglioside GM3 containing mixed lipid comprises 53% of a combination or mixture of two or more lipids selected from the group consisting of DPPC, DMPC and DSPC, 45% cholesterol, 1% PS, and 1% GM3, wherein the combination or mixture of lipids make up 51% of ganglioside GM3 containing mixed lipid layer.

In some embodiments of any method described, the combination or mixture of two or more lipids selected from the group consisting of DPPC, DMPC and DSPC can be in the ratio of 1:1:1, 3:1:1, 5:1:1, 4:1:1, 3:2:1, or 2:1:1.

In one embodiment of any method described, the ganglioside GM3 containing mixed lipid comprises ~51-52% DPPC, 45% cholesterol, 1% PS, ~1-3% GM3 and ~1-3% Gal-Cer.

In one embodiment of any method described, the ganglioside GM3 containing mixed lipid layer forms a lipid bilayer and comprises ~51-53% DPPC, 45% cholesterol, 1% PS, and ~1-3% GM3.

In one embodiment of any method described, the ganglioside GM3 containing mixed lipid layer forms a lipid bilayer and comprises 51% DSPC, 45% cholesterol, 1% PS, and 3% GM3.

In one embodiment of any method described, the ganglioside GM3 containing mixed lipid layer forms a lipid bilayer and comprises 52% DSPC, 45% cholesterol, 1% PS, and 2% GM3.

In one embodiment of any method described, the ganglioside GM3 containing mixed lipid layer forms a lipid bilayer and comprises 53% DSPC, 45% cholesterol, 1% PS, and 1% GM3.

In one embodiment of any method described, the ganglioside GM3 containing mixed lipid layer forms a lipid bilayer and comprises 51% of a combination or mixture of lipids selected from the group consisting of DPPC, DMPC and DSPC, 45% cholesterol, 1% PS, and 3% GM3, wherein the combination or mixture of lipids make up 51% of ganglioside GM3 containing mixed lipid layer.

In one embodiment of any method described, the ganglioside GM3 containing mixed lipid layer forms a lipid bilayer and comprises 52% of a combination or mixture of lipids selected from the group consisting of DPPC, DMPC and DSPC, 45% cholesterol, 1% PS, and 2% GM3, wherein the combination or mixture of lipids make up 52% of ganglioside GM3 containing mixed lipid layer.

In one embodiment of any method described, the ganglioside GM3 containing mixed lipid layer forms a lipid bilayer and comprises 53% of a combination or mixture of lipids selected from the group consisting of DPPC, DMPC and DSPC, 45% cholesterol, 1% PS, and 1% GM3, wherein the combination or mixture of lipids make up 52% of ganglioside GM3 containing mixed lipid layer.

In one embodiment of any method described, the ganglioside GM3 containing mixed lipid layer forms a lipid bilayer and comprises ~51-52% DPPC, 45% cholesterol, 1% PS, ~1-3% GM3 and ~1-3% Gal-Cer.

In one embodiment of any method described, the ganglioside GM3 containing mixed lipid layer forms a lipid monolayer and comprises 51-53% DPPC, 45% cholesterol, 1% PS, and 1-3% GM3.

In one embodiment of any method described, the ganglioside GM3 containing mixed lipid layer forms a lipid monolayer and comprises 51% DSPC, 45% cholesterol, 1% PS, and 3% GM3.

In one embodiment of any method described, the ganglioside GM3 containing mixed lipid layer forms a lipid monolayer and comprises 52% DSPC, 45% cholesterol, 1% PS, and 2% GM3.

In one embodiment of any method described, the ganglioside GM3 containing mixed lipid layer forms a lipid monolayer and comprises 53% DSPC, 45% cholesterol, 1% PS, and 1% GM3.

In one embodiment of any method described, the ganglioside GM3 containing mixed lipid layer forms a lipid monolayer and comprises 51% of a combination or mixture of lipids selected from the group consisting of DPPC, DMPC and DSPC, 45% cholesterol, 1% PS, and 3% GM3, wherein the combination or mixture of lipids make up 51% of ganglioside GM3 containing mixed lipid layer.

In one embodiment of any method described, the ganglioside GM3 containing mixed lipid layer forms a lipid monolayer and comprises 52% of a combination or mixture of lipids selected from the group consisting of DPPC, DMPC and DSPC, 45% cholesterol, 1% PS, and 2% GM3, wherein the combination or mixture of lipids make up 52% of ganglioside GM3 containing mixed lipid layer.

In one embodiment of any method described, the ganglioside GM3 containing mixed lipid layer forms a lipid monolayer and comprises 53% of a combination or mixture of lipids selected from the group consisting of DPPC, DMPC and DSPC, 45% cholesterol, 1% PS, and 1% GM3, wherein the combination or mixture of lipids make up 52% of ganglioside GM3 containing mixed lipid layer.

In one embodiment of any method described, the ganglioside GM3 containing mixed lipid layer forms a lipid monolayer and comprises 51% DPPC, 45% cholesterol, 1% PS, 3% GM3 and 3% Gal-Cer.

In one embodiment of any method described, the sonication period is about 5 sec to 45 min. In other embodiments, the sonication period is about 5 sec to 40 min, about 5 sec to 30 min, about 5 sec to 25 min, about 5 sec to 20 min, about 5 sec to 15 min, about 5 sec to 10 min, about 5 sec to 5 min, about 5 sec to 4 min, about 5 sec to 3 min, about 5 sec to 2 min, about 5 sec to 1 min, about 5 sec to 30 sec. In one embodiment of any method described, the sonication period is about 5 seconds. In one embodiment of any method described, the sonication period is about 30 minutes.

In one embodiment of any method described, the pore size for extruding the ganglioside GM3-mixed lipid nanoparticles is in the range of 100-200 nm, 100-150 nm, or 100-175 nm.

In one embodiment of any method described, the lipid further comprises a labeling agent. For example, a fluorescent dye for imaging, tracking and detection. Non-limiting examples include lipophilic fluorescent dyes such as DiI, DiO, DiD, DiA, and DiR (INVITROGEN™).

Self-assembled biomimetic nanosystems with defined surface properties represent engineerable model systems for characterizing the role of specific surface functionalities in virus-host cell interactions. The inventors have used this approach to validate the role of GM3 in the viral envelope glycoprotein-independent binding and cellular trafficking of HIV-1 via a reverse engineering approach. The inventors observations that GM3 loaded AVNs are sequestered into the same compartments as VLPs and that these compartments are associated with tetraspanins provide experimental evidence for an imitation of virus particle behavior by AVNs.[61,62] The successful mimicry of HIV-1 trafficking mechanisms in monocyte-derived DCs and HeLa/CD169 cells with AVNs that contain only GM3 as a potential ligand unambiguously confirms the hypothesis that GM3 is the non-virus encoded surface functionality that facilitates an envelope protein-independent capture of HIV-1 particles. Since the AVNs generated in this work share similarities with GM3 presenting exosomes,[7,9] the inventors findings are consistent with the Trojan exosome hypothesis[65] that HIV has parasitized host intercellular vesicle trafficking pathways to enhance its dissemination.

The inventors implemented two types of GM3-containing AVNs, one containing a complete lipid bilayer membrane (AVN1) and the other containing a single lipid layer grafted onto the NP surface through hydrophobic interactions (AVN2). The fact that both GM3 functionalized AVN1 and AVN2 bind to HeLa/CD169 but not HeLa cells confirms that CD169 is the receptor for nanoconjugated GM3, independent of its presentation in a lipid monolayer or bilayer. Both types of AVNs were found to elicit a unique spatial sequestration in both HeLa/CD169 and mature DCs. Based on the particle distribution obtained by darkfield imaging, AVN clustering occurs preferentially in peripheral cell areas for both mature DCs and HeLa/CD169 cells. Combined SEM/FIB investigations in HeLa/CD169 cells substantiated this finding by revealing an accumulation of AVN clusters within tens of nanometers below the plasma membrane. In principle, this enrichment of the AVNs in direct vicinity of the plasma membrane could be the result of an exocytic intracellular pathway that directs a significant fraction of endocytosed AVNs from multivesicular endosomes to the plasma membrane via exosomes, especially in immature DCs.[7,66] Recent studies have, however, questioned, the role of the exocytic mechanisms in the peripheral sequestration of HIV in mature DCs[67] and, instead, suggested capture and retention of virus in solvent accessible plasma membrane invaginations.[62,68] While the localization of virus particles in solvent accessible membrane invaginations is considered essential for efficient inter-cell transfer of viral particles during trans-infection,[62] the mechanism by which CD169 traffics virus particles to these peripheral compartments remains unclear. Independent of the exact mechanisms underlying the collection of AVNs in peripheral clusters, the fact that the GM3 containing minimalistic AVNs induce this unique spatial distribution in HeLa/CD169 cells provides experimental evidence in support of the hypothesis that GM3-CD169 interactions play a key role in orchestrating the cellular response of DCs during HIV-1 trans-infection.[8,9,9,12,13,69] Interestingly, GM3-CD169 binding can induce this cellular program despite the absence of any previously defined endocytotic motifs in the cytoplasmic tail of CD169.[70] The dynamics of the spatial sequestration of AVNs and VLPs in HeLa/CD169 cells was found to be slower and the extent less significant than in mature DCs. VLP/AVN clustering in peripheral compartments in HeLa/CD169 cells was apparent at 20 h post VLP/AVN exposure. The lack of endocytotic motifs in the cytoplasmic tail of CD169, together with the observation that the sequestration kinetics of AVNs are significantly faster in mature DCs (within 1 h) than in HeLa/CD169, points towards the existence of yet to be identified membrane associated co-factors or mechanisms that accelerate virus uptake and processing after GM3-CD169 engagement in mature DCs.

The fact that in HeLa/CD169 a sequestration was observed for GM3 containing AVNs but not for GM3 functionalized liposomes indicates that the presentation of GM3 is necessary but not sufficient to trigger sequestration. One striking difference between AVNs and liposomes of identical size and membrane composition is the difference in structural stiffness. Liposomes[57] are much softer than HIV virions[39] or metal NP[56] containing AVNs. One conclusive rationalization of the differences between liposomes and AVNs is, therefore, that mechanical properties also influence the intracellular fate of virus particles and that—unlike the AVNs—the liposomes are too soft to induce the sequestration observed for the virus. The observed differences in the spatio-temporal distribution of AVNs and liposomes argue in favor of AVNs as the more realistic model system for validating the potential role of specific membrane functionalities in the HIV-1 trans-infection mechanism.

The experimental validation that GM3 functionalized AVNs successfully mimic viral behavior has important implications beyond elucidating fundamental mechanistic details of the GM3-CD169-mediated transfection pathway. A selective capture of GM3-AVNs by CD169 paves the path to new delivery strategies that can selectively deliver drugs and vaccines to CD169 expressing DCs and macrophages in vivo, which are key components of the immune system. Furthermore, our experimental findings show vividly that in contrast to endocytosis and targeting to lysosomal compartments, alternative cellular uptake and trafficking mechanisms can be targeted by smart NPs with rationally designed lipid membrane surfaces. The successful mimicry of HIV-1 sequestration into peripheral non-lysosomal compartments, an evolutionary optimized viral strategy for avoiding lysosomal degradation, forms the basis for novel AVN-based delivery strategies that can minimize the intracellular degradation of sensitive cargo. Due to their ability to target key cells of the immune system and to initiate non-lysosomal uptake routes, GM3 functionalized AVNs can contribute significantly to overcome key challenges in drug delivery.

The present disclosure can be defined in any of the following numbered paragraphs:

[1] A nanoparticle comprising: a core having a largest diameter between 50-90 nm; a coating layer encasing the core; and a ganglioside GM3-containing mixed lipid layer comprising of dipalmitoylphosphatidylcholine (DPPC), cholesterol, phosphatidylserine (PS), and aNeu5Ac(2-3)bDGalp(1-4)bDGlcp(1-1)Cer (GM3); wherein the ganglioside GM3-mixed lipid layer is exterior of the coating layer and is integrated into the coating layer, and wherein the nanoparticles have an overall particle size between 60-100 nm.

[2] The nanoparticle of paragraph 1, wherein the core is a solid core.

[3] The nanoparticle of paragraph 1 or 2, wherein the core is has a shape that is selected from the group consisting of ellipsoid, spherical, rod-like, octahedral, and cube-like.

[4] The nanoparticle of any one of paragraphs 1-3, wherein the core comprises a material selected from the group consisting of gold, silver, a gold alloy, a silver alloy, silica, mesoporous silica, polystyrene, and titania.

[5] The nanoparticle of any one of paragraphs 1-4, wherein the coating layer is a thiolated lipid.

[6] The nanoparticle of paragraph 5, wherein the thiolated lipid comprises long-chain thiol-terminated alkanes.

[7] The nanoparticle of paragraph 6, wherein the thiolated lipid is selected from the group consisting of octodecanethiol, hexadecane thiol, heptadecane thiol, and octadecane.

[8] The nanoparticle of any one of paragraphs 1-4, wherein the coating layer is a silane with long alkyl chains.

[9] The nanoparticle of paragraph 8, wherein the silane is octadecylsilane.

[10] The nanoparticle of any one of paragraphs 1-4, wherein the coating layer is polyethylene glycol thiol.

[11] The nanoparticle of any one of paragraphs 1-10, wherein the ganglioside GM3 containing mixed lipid layer consists of 40%-60% of DPPC.

[12] The nanoparticle of any one of paragraphs 1-10, wherein the ganglioside GM3 containing mixed lipid layer consists of 40%-60% of cholesterol.

[13] The nanoparticle of any one of paragraphs 1-10, wherein the ganglioside GM3 containing mixed lipid layer consists of 0.5%-5% of PS.

[14] The nanoparticle of any one of paragraphs 1-10, wherein the ganglioside GM3 containing mixed lipid layer consists of 0.1%-6% of GM3.

[15] The nanoparticle of any one of paragraphs 1-10, wherein the ganglioside GM3 containing mixed lipid layer optionally consist of galactosylceramide (Gal-Cer).

[16] The nanoparticle of any one of paragraphs 1-10, wherein the ganglioside GM3 containing mixed lipid layer consists of DPPC, cholesterol, PS, and GM3, and optionally Gal-Cer.

[17] The nanoparticle of any one of paragraphs 1-10, wherein the nanoparticle comprises a second layer of ganglioside GM3 containing mixed lipid.

[18] A method of delivering a nanoparticle into a cell comprising adding a nanoparticle of any one of paragraphs 1-17 to a CD169-expressing eukaryotic cell under conditions that permit the nanoparticle to be endocytosed into the CD169-expressing eukaryotic cell, and waiting for a sufficient time for endocytosis to occur.

[19] The method of paragraph 18, wherein the CD169-expressing eukaryotic cell is a Hela cell, a dendritic cell or a macrophage.

[20] The method of paragraph 18 or 19, wherein the nanoparticle is sequestered within non-lysosomal tetraspanin-positive compartments of the CD169-expressing eukaryotic cell.

[21] A pharmaceutical composition comprising a nanoparticle of any one of paragraphs 1-17 in a physiologically acceptable carrier.

[22] A method of making a nanoparticle of paragraph 1 comprising: (a) contacting a core nanoparticle with a coating layer material to coat the particle; (b) adding the coated core nanoparticle to a ganglioside GM3 containing mixed lipid solution; (c) sonicating the contacted mixture of step (b) for a period of time; (d) extruding the particles from step (c) through a membrane with a pore size of about 100-200 nm; and (e) collecting the extruded nanoparticles from the membrane.

[23] A method of making a nanoparticle of paragraph 1 comprising: adding a thiolated lipid to a core particle to coat the particle; sonicating a ganglioside GM3 containing mixed lipid solution for a period of time to form liposomes; adding the thiolaled lipid coated particle of step a to the liposomes of step b; and collecting nanoparticles formed.

[24] A method of studying the interaction between CD169+ dendritic cells or macrophage and CD4+ T cells comprising: contacting a CD169+ dendritic cell or macrophage with a nanoparticle of any one of paragraphs 1-17; allowing the nanoparticle to be taken up into the CD169+ dendritic cell or macrophage; contacting the cell of step b with a CD4+ T cells; and observing the interaction between the CD169+ dendritic cell or macrophage and the CD4+ T cell.

This disclosure is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the disclosure described herein. Such equivalents are intended to be encompassed by the following claims.

EXAMPLE

GM3 has recently been recognized as a highly efficient ligand for CD169 which is selectively expressed on activated macrophages and dendritic cells. The relatively weak binding strength between GM3 and CD169 requires multivalent interactions to achieve efficient binding. In this disclosure, the inventors describe a unique nanoparticle platform that embeds GM3 in a fluid lipid monolayer wrapped around a solid core that achieves multivalent GM3 presentation and retains a high degree of mobility of the ligand ensuring that multiple ligands on one nanoparticle can interact with several receptors on a target cell. The macrophage/dendritic cell targeting mechanism is based on a small lipid that is common in humans and, therefore, is not expected to result in a strong immune response. The disclosure describes a nanoparticle that combines the biological functionality of a membrane with the imaging properties of a metal core, making the materials interesting for mechanistic, therapeutic and diagnostic applications.

Materials and Methods

AVN1 Preparation 1 ml $1.1 \times 10^{10}$ particles/ml colloidal Au NPs with a nominal diameter of 80 nm (Ted Pella) were incubated with 5 μl 10 mM polyethylene glycol thiol propionic acid overnight, followed by 3 cycles of washing through centrifugation (2500 rpm 10 min) and re-suspension in ddi water to remove excess acid-PEG. The functionalized Au nanoparticles (Au NPs) were resuspended into 1 ml 10 mM NaCl, pH=7. Simultaneously, a total amount of 1 mole of lipid mixture (Avanti Polar Lipids, Alabaster, Ala.) was dissolved in 100 μl chloroform (for lipid mix composition see FIG. 1b) in a clean 25 ml round-bottom flask. The lipid mixture was then sonicated for 5 s, followed by rotary evaporation for 15 min. A uniformly thin lipid dry layer formed on the bottom of the flask, which was further dried under vacuum overnight. The above acid-PEG functionalized Au NPs solution was injected into the flask through a disposable syringe to rehydrate the lipid film in the presence of Au NPs at 50° C. for 1 h. Subsequently, 30 min sonication was applied to agitate the suspension and maximize lipid hydration. Immediately after sonication, the lipid-Au NP mixture was transferred into a cryo-vial under Ar protection, and underwent 3 freeze-thaw cycles in liquid nitrogen and 50° C. water. After another sonication step of 30 min, the solution was extruded through a 200 nm-pore-size polystyrene membrane with a mini-extruder set (Avanti Polar Lipids). AVNs were then purified from free liposomes through 3 cycles of centrifugation (2500 rpm, 10 min), and resuspended in 100 μl 10 mM NaCl for further use.

AVN2 Preparation

A thin dry layer of lipid mixture was prepared following the procedures described for AVN1. 1 ml of 20 mM HEPES buffer (pH=7.2) was then added, forming a cloudy solution after vigorous agitation. The mixture was then sonicated for 30 min in ice bath until the solution became clear. This liposome solution was then stored in 4° C. for further use. 1 ml 100 nm colloidal Au NP solution ($1.1 \times 10^{10}$ particles/ml) was pelleted via centrifugation at 2500 rpm for 10 min. 0.5 ml of the prepared liposome solution was added to the Au pellet, and the volume was increased to 1 ml with 20 mM HEPES buffer. 200 μl of 0.01 mg ml-1 1-octodecane-thiol solution in ethanol was then added dropwise to the mixture. The mixed solution was agitated overnight on a rotator. After that, the AVNs were washed three times through centrifugation (2500 rpm, 10 min) and resuspension in ddi water. Finally, the AVN pellet was resuspended in 100 μl 20 mM HEPES buffer and ready to use.

TEM Characterization of AVNs

AVN stock solutions were diluted to approximately $1 \times 10^7$ AVNs/ml with ddi water and drop-cast onto carbon coated TEM grids. Excess solution was removed by a clean filter paper after 1 min incubation, and the samples were dried and stored in vacuum before imaging using a JEOL JEM 2010 HRTEM with 200 kV HT.

UV-VIS

Spectra of diluted AVN solutions ($1 \times 10^7$ particles/ml) in 10 mM NaCl (pH=7.0) were acquired on an Agilent Cary 5000 UV/VIS spectrometer. 10 mM NaCl was used for baseline correction. All spectra were normalized relative to their peak maxima.

Dynamic Light Scattering and Zeta Potential Measurements

Measurements were performed on a Zetasizer Nano ZS90 (Malvern, Worcestershire, U.K.). AVNs were diluted to $1 \times 10^7$ particles/ml with 10 mM NaCl (pH=7.0).

Cells and Cell Culturing

HeLa/CD169 cells stably expressing CD169 were established by transduction with VSV-G pseudotyped LNC-CD169 retroviral vector as described in Izquierdo-Useros et al[7].

CD169 expression was confirmed by flow cytometry and immunofluorescence assay with Alexa-647 conjugated anti-CD169 antibody (AbD-Serotec; 1:50 dilution). Note that ~60% of cells expressed CD169.

To generate CD169-mCherry fusion protein, the ApaI-XbaI fragment containing 3' half of CD169 from LNC-CD169 was subcloned into the pSL1180 vector (GE Healthcare Life Science), and the stop codon of CD169 mutated to glycine (from TGA to GGA) by PCR using the following primers, CD169-4188-F (5'-ATCAGGGACAGGCCAT-GTCC-3') (SEQ ID NO: 1) and CD169-stop-R (5'-AC-CTCTAGACAACACCACTGGTCCGCCCAGG-3') (SEQ ID NO: 2). The mutagenized fragment was cloned back into the corresponding region of CD169 in LNC-CD169 using SbfI and XbaI restriction sites. To create an XbaI site at the 5' end of the mCherry gene, the mCherry gene was amplified from Gag-mCherry-encoding plasmid7 by PCR using the following primers, GFP-5-XbaI-F (5'-AAAAAATCTA-GAATGGTGAGCAAGGG-3') (SEQ ID NO: 3) and Gag-eGFP-N-R (5'-AACCTCTACAAATGTGGTATGG-3') (SEQ ID NO: 4). The PCR-amplified mCherry gene was digested with XbaI and NotI, and cloned in frame into the C-terminal end of the stop-codon-mutated-CD169 (LNC-CD169-mCherry).

HeLa cells were transduced with LNC-CD169-mCherry retroviral vector as previously described,[7,13] selected and maintained in the presence of 0.5 mg ml$^{-1}$ G418. Both HeLa/CD169 cells and HeLa/CD169-mCherry cells were cultured in 10% FBS, 1% penicillin streptomycin, and 0.5 mg/ml G418 containing Dulbecco Modified Eagle Medium (DMEM). Primary monocyte derived DCs were differentiated from CD14+ peripheral blood monocytes and matured with LPS (100 ng ml$^{-1}$) for 2 days as described elsewhere[7,13].

Both HeLa/CD169 cells and HeLa/CD169-mCherry cells were cultured in 10% FBS, 1% penicillin streptomycin, and 0.5% G418 containing Dulbecco Modified Eagle Medium (DMEM).

VLP Generation

HIV Gag-eGFP VLPs were obtained by transfection of HEK293T cells with the pGag-eGFP plasmid expressing codon-optimized Gag-eGFP fusion protein as described previously.[13]

AVN and VLP Binding and Sequestration

Prior to exposure to AVNs or VLPs, HeLa/CD169 cells were seeded on 24×60 mm$^2$ coverslips and cultured to 30-40% confluency. The cell coverslips were then briefly rinsed with warm Hank's buffer (no $Ca^{2+}/Mg^{2+}$). AVNs or VLPs were diluted to $5 \times 10^8$ particles/ml (AVN) or $1 \times 10^{10}$ particles/ml (VLPs) with DMEM, and 1 ml of diluted AVNs or VLPs was added to the coverslips and incubated at 37° C. for the specified time in a water saturated atmosphere with 5% $CO_2$. Excess AVNs or VLPs were subsequently removed by washing with warm Hank's buffer for 3 times. For binding studies the cells were then fixed with 4% paraformaldehyde and imaged. In experiments monitoring the temporo-spatial redistribution of the AVNs or VLPs, excess particles were removed after 10 min incubation and the cells were re-immersed into complete growth medium and further incubated at 37° C. After 20 h, the cells were treated with 100 nM Lysotracker Deep Red (INVITROGEN) and nucleus stain Hoechst 33342 for 30 min at 37° C. Samples were then washed with Hank's buffer and fixed by 4% paraformaldehyde for 15 min at room temperature and subsequently imaged.

For DC samples, AVNs were incubated with DCs for 1 h at 37° C., and washed with 1×PBS buffer by centrifugation for 3 times. Cells were then fixed by 4% paraformaldehyde and cytospun onto poly-L-lysine (SIGMA) treated glass coverslips. For co-localization of GM3-AVNs and HIV Gag-eGFP VLPs in mDCs, cells were challenged with $10^7$ AVN2 particles and 5 ng of VLPs for 1 h at 37° C., washed, fixed with 4% paraformaldehyde and processed for imaging as described above. To determine if GM3-AVN2 were co-localized with CD81 in mDCs, cells were challenged with 107 AVN2 for 1 h at 37° C., fixed with 4% PFA, permeabilized with 0.5% Triton X-100, blocked with 20% normal human serum (NHS), and stained with α-CD81 mAb (BD; 1:50 dilution) and detected with ALEXA488-conjugated 2°Ab (INVITROGEN; 1:50 dilution), as described previously[13].

For SEM/FIB microscopy, cell samples were fixed with 2.5% glutaraldehyde solution for 15 min at room temperature and dehydrated by gradient concentrations of acetone (30%, 50%, 70%, 95%, 100%, 15 min each) and subsequent vacuum drying. Samples were stored in desiccators and sputter-coated with 5 nm Au/Pd prior to SEM/FIB.

Image Recording and Data Processing

Figure 7:
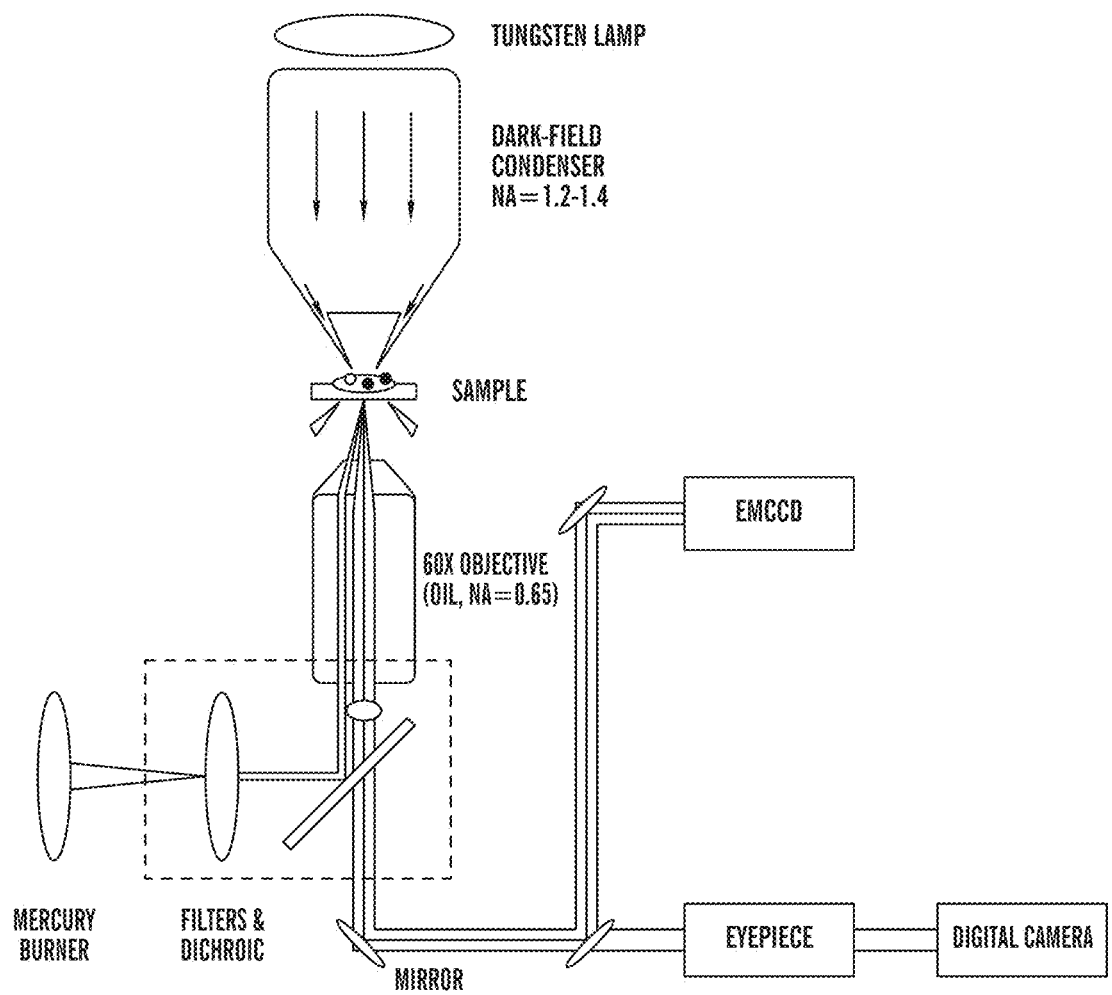
FIG. 7 shows the optical Imaging Set-up. The samples are illuminated by a tungsten light source through a high NA condenser for darkfield imaging, or by a mercury burner with suitable filter/dichroic cubes for fluorescence microscopy. Using a mirror, the light path can be switched between two channels (darkfield or fluorescence). Scattered light or fluorescent signals are collected through a 60× objective (oil, NA=0.65), and recorded by either an EMCCD camera (Andor) or a Nikon D900 SLR digital camera through an eyepiece adapter.

All optical imaging experiments were performed on an Olympus IX71 inverted microscope (see FIG. 7). Images were taken with a 60× oil objective with variable NA (NA=0.65-1.25). For darkfield imaging the samples were illuminated with a 100 W tungsten lamp through a high NA oil darkfield condenser (NA=1.2-1.4). Darkfield images were recorded with an Olympus SP310 digital camera or Nikon D3100 SLR connected to the microscope through an eyepiece adapter. Fluorescence imaging was performed under epi-illumination using appropriate filter sets. Images were recorded with an Andor Ixon+ electron multiplying charge coupled device detector (EMCCD). The NA of the collecting objective was adjusted for darkfield and fluorescence imaging to optimize signal-to-noise. The recorded images were further processed by ImageJ for coordinates alignment and overlay.

SEM/FIB and Correlation with Optical Microscopy

Cell dishes intended for characterization through SEM/FIB were diced into 1 cm×1 cm squares, and covered by a SEM finder grid (SEMF2, copper, Ted Pella). The grid was immobilized through super glue. Ethanol was dropped onto the sample to locate cells of interest in dark-field microscopy. The samples were then dried, and sputter coated with a ~5 nm thick Au/Pd layer to increase conductivity. Samples were kept in desiccators until they were transferred into the SEM/FIB. To mount the sample, conductive copper tape was used to attach the coated sample onto SEM stub, and carbon paint was used to increase conductivity. Samples were imaged first using a Zeiss Supra40VP SEM at 2.0 kV and a working distance of 6 mm. The samples were subsequently milled and imaged with an FEI Quanta 3D FIB instrument. The milling was done with 30 kV 0.5 nA Gallium ion beam with 20 s intervals. The estimated milling depth per step was calibrated by applying the same milling on a spin coated PMMA chip and measuring the resulting depth with a Zygo Optical Profiler (New View 6300).

Results

Design and Fabrication of Artificial Virus Nanoparticles (AVNs)

Figure 1B:
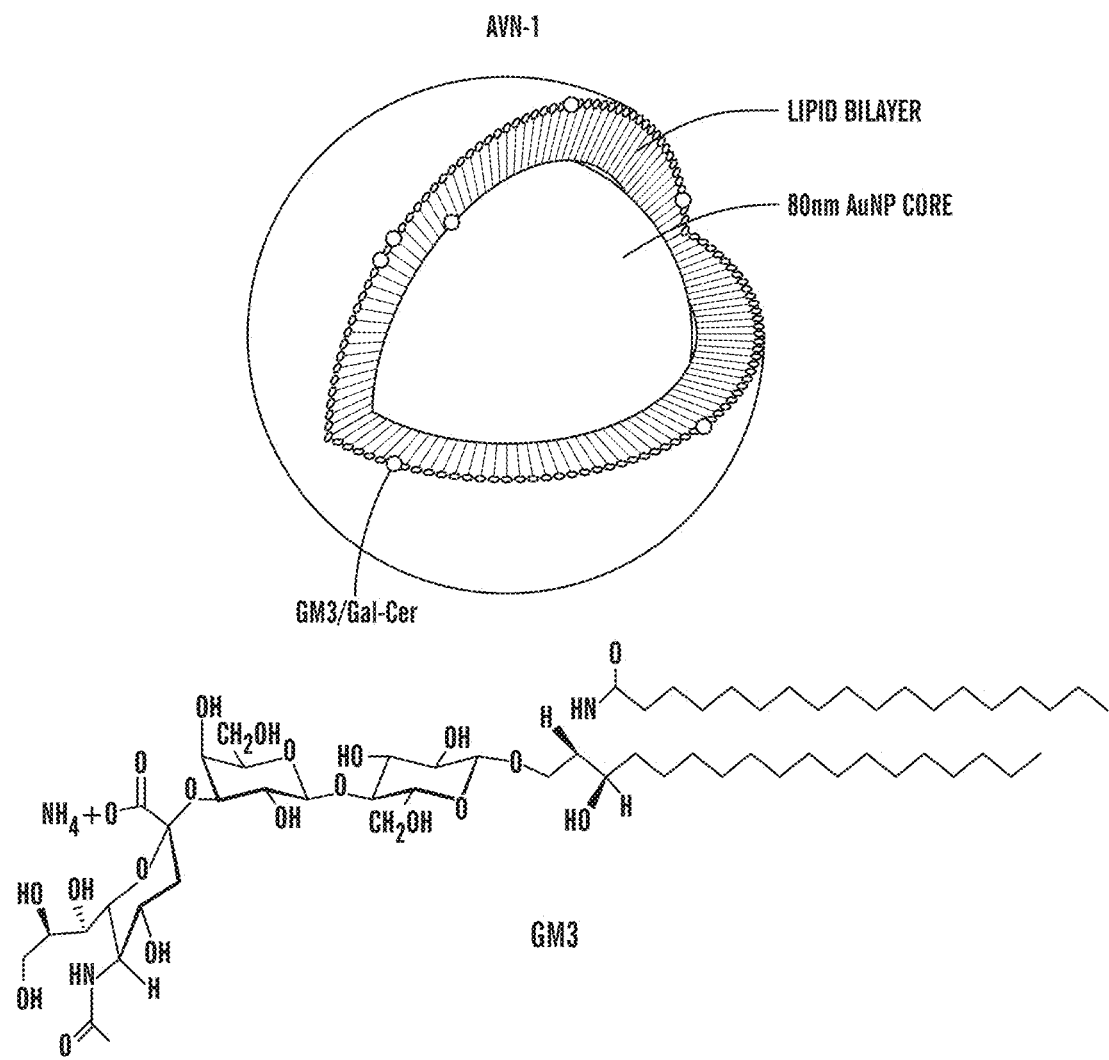
Figure 1B:
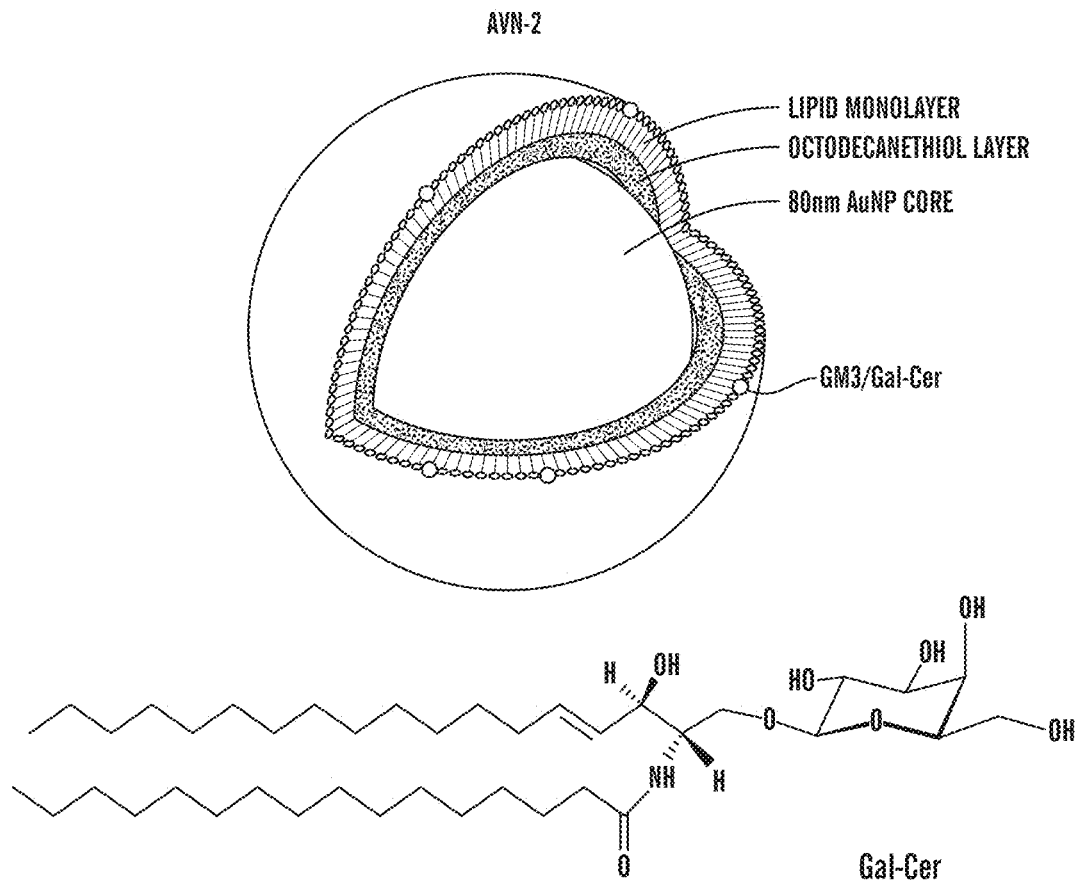

HIV-1 particle assembly and budding can occur upon expression of Gag alone in the absence of other viral proteins in host cells. The mature virus particle has a typical size between 120-150 nm,[34,35] contains 2500 Gag molecules, and is wrapped in a lipid bilayer that the virus acquires from the plasma membrane during budding from the host cell (reviewed in ref36). The Gag polyprotein is proteolytically cleaved into six structural proteins, matrix (MA), nucleocapsid (NC), capsid (CA), p6 and two spacer proteins, SP1 and SP2 during the virus maturation step.[37] Schematic illustrations of the mature virus structure containing the MA protein-enclosed CA shell with the NC-coated viral RNA and the AVN models to mimic it are shown in FIGS. 1a and 1b, respectively. The inventors' AVN design is based on a self-assembled lipid layer around an 80 nm diameter noble metal nanoparticle (NP) that serves as analogue of the lipid enclosed core formed by association of basic amino acid residues in MA with the inner leaflet of the phosphatidylinositol (PI) 4,5-bisphosphate [PI(4,5)P2] enriched lipid bilayer.[36] The lipid layer emulates the virus membrane but is entirely free of proteins and can be engineered with a defined lipid composition, ligand density, and controllable surface charge. In this work the inventors are particularly interested in GM3 containing AVNs for a selective investigation of GM3 interactions with CD169 under well-defined conditions in the absence of potential interferents. Au were chose as core material since it provides the assembled AVNs with mechanical stiffness[38,39] and, at the same time, allows high contrast optical imaging in optical, electron, and x-ray microscopy.[40,41] The optical response of spherical Au NPs is dominated by localized surface plasmon resonances (LSPRs) in the visible range of the electromagnetic spectrum.[42] A resonant excitation of the LSPR in an 80 nm Au NP is associated with a scattering cross-sections of approximately $\sigma \approx 2.3 \times 10\text{-}10$ cm2.43 This huge elastic scattering efficiency, which is orders of magnitude larger than conventional fluorescence cross-sections, facilitates single particle detection entirely free from blinking or bleaching in conventional darkfield microscopy.[41,44] Their unique photophysical stability together with their programmable surface properties make Au NPs the core of choice for AVNs in optical studies.

Different experimental strategies have been developed for creating lipid layers around NP cores with different sizes.23, 45-49 For the relatively large NPs of the AVN design, two strategies in particular are promising (see Methods section and FIG. 4). Strategy 1 (51) is based on a lipid encapsulation approach that traps Au NPs within unilamellar vesicles.[46] Strategy 2 (S2) incorporates the lipids with their hydrophobic tail into an octodecane-thiol brush assembled on the surface of Au NPs.[45] While 51 leads to a complete bilayer membrane, S2 embeds a single layer of lipids into a self-assembled monolayer of octodecane-thiols through their hydrophobic lipid tails. Both, S1 and S2, achieve a presentation of GM3 on the AVN surface with the sialic acid containing sugar head group pointing into the solution. In the following, the inventors refer to the artificial virus nanoparticles obtained through these two strategies as AVN1 and AVN2, respectively. Although S2 is synthetically simpler and more efficient than S1, lipid mobility and density obtained via S2 are anticipated to differ from those of the native bilayer membrane of enveloped virus particles.

HIV-1 preferentially buds from lipid rafts so that the host-derived viral membrane is enriched in lipids with saturated fatty acids, GSLs,[50] and cholesterol.[51] The membrane composition for the AVNs was simplified and comprised a limited number of lipids of comparable size that provide similar physico-chemical properties as the virus membrane. The compositions of the viral membrane and of the AVN membranes used in this work are summarized in Table 1. The inventors chose dipalmitoylphosphatidylcholine (DPPC) containing two hydrophobic fatty acid chains and cholesterol as main components of the investigated membranes and integrated small quantities of phosphatidylserine (PS) to provide a negative surface charge comparable to that on HIV-1 particles.[52,53] In addition, TopFluor-labeled cholesterol molecules were incorporated into the membrane to monitor AVN formation via fluorescence microscopy. Either 3 mol % GM3 or α-Galactosyl Ceramide (Gal-Cer) were added to test the role of these lipids for binding CD169. The inventors included Gal-Cer as control in the studies since it is chemically similar to GM3 but does not contain any sialic acid residues and, thus, was shown previously to not bind CD169.8

Characterization of AVNs.

Figure 5:
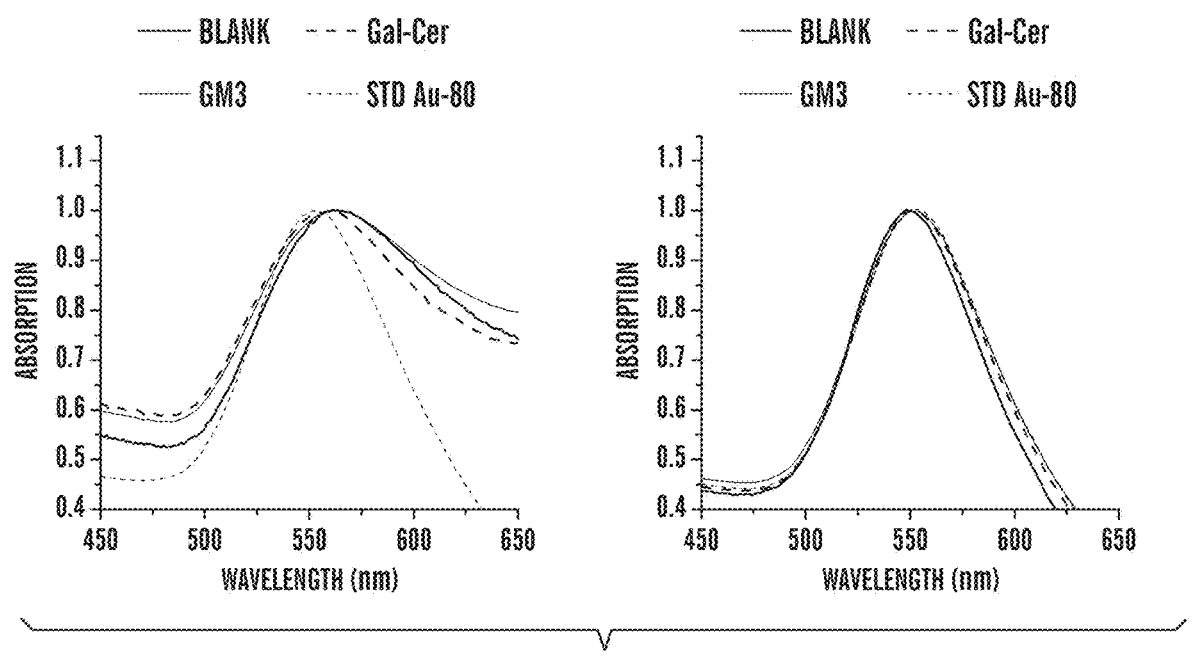
FIG. 5 shows the UV-VIS spectra of AVN1 (left) and AVN2 (right). Blank, Gal-Cer, and GM3 particles of type AVN1 have peak resonance wavelengths of 561 nm, which compares with 550 nm for citrate stabilized 80 nm Au NPs. The peak wavelengths for blank, Gal-Cer, and GM3 functionalized particles of type AVN2 are 553 nm.
Figure 6:
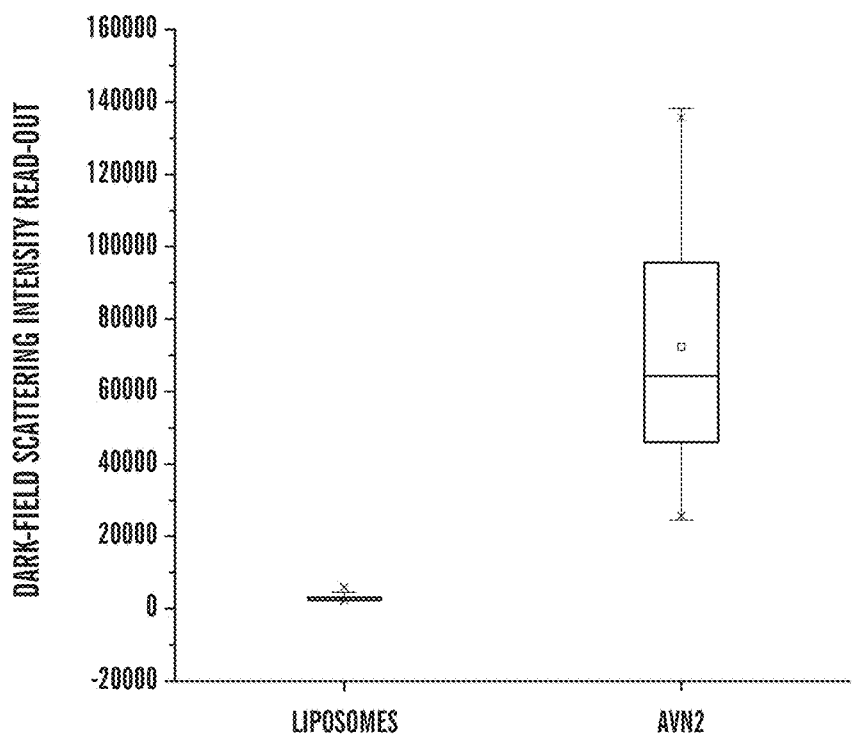
FIG. 6 shows the box plot of the intensity distribution of AVN2 and liposomes with comparable sizes under the same darkfield image setup and recording conditions. AVNs are at least 10 fold brighter than liposomes.

The inventors characterized the generated AVNs by measuring their hydrodynamic radii and zeta potentials (FIG. 2a-2b). The hydrodynamic radius, reported as the peak in the size distribution obtained through dynamic light scattering, for GM3 containing AVN1 is rhyd(AVN1)=77.8±5.3(s.d.) nm compared to rhyd(AVN2)=50.7±3.0(s.d.) nm for GM3 containing AVN2. The observed difference in rhyd between AVN1 and AVN2 is too large to be accounted for only by differences in the membrane shell. Instead, the measured size difference indicates some self-association of the 80 nm Au NPs in the case of AVN1. Consistent with an increased level of NP clustering,[41,54,55] the UV-Vis spectra (see FIG. 5) confirm a red-shift of the ensemble-averaged plasmon resonance wavelength of approximately 8 nm for AVN1 when compared with AVN2. Both of the AVNs have zeta potentials between −20~−30 mV, which is close to the published value for HIV-1 particles of −20 mV under identical experimental conditions.[52] Due to their resonant interaction with the incident light, the Au NPs used in this work are extraordinarily bright and have a characteristic green-orange color. Liposomes and other organic contaminations with comparable sizes, in contrast, are dim (see FIG. 6) or appear as broadband scatterers, which makes them easily discernable from metal NPs. Correlated darkfield/fluorescence microscopy (see FIG. 7) is, therefore, an appropriate method for validating successful lipid wrapping around the NPs. Darkfield and fluorescence images of surface-immobilized AVN1 and AVN2 for representative preparations are taken. Consistent with a successful formation of AVNs that contain both lipid and noble metal NP components, the images show >90% colocalization of fluorescence and darkfield signals for all AVN preparations. The exact colocalization statistics for approximately 1000 particles of each type are summarized in the FIGS. 2c and 2d. Darkfield image and fluorescence image of 80 nm AuNP after overnight incubation with octodecanethiol-ethanol solution together with topfluor-cholesterol dye, but no lipids. After surface immobilization and washing, no signal is observed from the topfluor dye channel. This finding proves that there is no significant non-specific adsorption of the dye molecule to the octodecanethiol coated particle surface in the absence of an intact membrane structure. Control experiments performed with pegylated Au NPs incubated with TopFluor cholesterol in the absence of lipids did not yield any measurable fluorescence signal (Data not shown).

High resolution TEM images of AVN1 and AVN2 (FIGS. 2e-2f) show a distinct corona around the NPs, which is additional proof of successful membrane assembly around the NPs. For AVN2 the corona is 4-5 nm thin. Together with the small difference between rhyd(AVN2) and the hydrodynamic radius of the citrate stabilized Au NPs (rhyd=49.0±1.2 (s.d.) nm), the thin corona indicates the addition of a single lipid layer to the octadecane thiol functionalized NPs in the AVN2 assembly process.

Consistent with the larger rhyd and relative spectral red-shift for AVN1 when compared with AVN2, the TEM images show mostly small clusters for AVN1, whereas for AVN2 individual Au NPs are predominantly observed. Although AVN1 preparations show some partial NP self-association, the average sizes of both AVN1 and AVN2 overlap with the natural size distribution of a HIV-1 virion. The inventors concluded that based on the physical parameters of size, shape, and surface charge, both S1 and S2 represent viable synthetic strategies for AVNs.

The inventors also tested the mechanical stiffness of individual VLPs and AVN2 particles through atomic force microscopy (AFM) nanoindentation measurements and found that AVN particles are stiffer than VLPs or liposomes. These findings are consistent with previous nanoindentation studies which reported a Young's modulus in the few GPa range and above[56] for biomolecule loaded Au NPs and Young's moduli of ~950 MPa or ~440 MPa for immature and mature HIV virions,[39] respectively. Liposomes are softer than both AVNs and virus particles; egg-PC cholesterol liposomes, for instance, have a Young's modulus of ~11 kPa.57

GM3-Mediated Temporo-Spatial Distribution of VLPs

VLPs are currently the model systems of choice for investigating the viral glycoprotein-independent capture of HIV-1 particles:[7-9] whose behavior defines logical benchmarks for the evaluation of our reverse engineering strategy. Spatial redistribution of HIV Gag-eGFP VLPs after binding to HeLa/CD169 cells. The VLPs selectively bind to HeLa/CD169 cells but not to parental HeLa cells after 10 min of incubation. 20 h after binding to HeLa/CD169 the initially randomly distributed VLPs are enriched in peripheral compartments that do not co-stain with Lysosome Tracker. Fluorescence images of CD169-mCherry, VLP, and overlay 20 h after initial incubation with HIV Gag-eGFP VLPs. The fluorescence data show a strong optical colocalization of CD169 and VLPs. The VLP segregation was confirmed in two independent imaging experiments.

In a first round of calibration experiments, the inventors evaluated the binding specificity of VLPs in HeLa cells transduced to constitutively express CD169 (HeLa/CD169). Cells were incubated for 10 min with $1 \times 10^{10}$/mL VLPs in DMEM, washed and transferred to the fluorescence microscope for an optical inspection of the binding.

The inventors found that VLPs bound efficiently to HeLa/CD169 (Data not shown) but not to CD169-negative parental HeLa cells (Data not shown). This selective binding confirms that VLP binding is CD169 specific. Previous studies by Puryear et al and Izquierdo-Useros et al have demonstrated that GM3-mediated interactions of VLPs and infectious HIV-1 particles with CD169 on mature DCs induced a polarized virus distribution that resulted in an accumulation of the particles in non-lysosomal focal spots with preferential localization at the cell periphery.[7,9,13] This characteristic spatial distribution was typically observed within 1-2 hours after virus binding with the exact time depending on the particle concentration. Interestingly, the inventors observed a similar clustering of VLPs in HeLa/CD169 only when the cells were cultured for additional time after exposure to the VLPs. While the VLPs are initially randomly distributed across the surface of HeLa/CD169 cells (Data not shown), they experience a spatial redistribution as a function of time. In approximately ⅓ of the cells, this redistribution culminates after 20 h in a strong local enrichment of VLPs in spatially confined spots. In good agreement with previous observations in DCs,[7,9,13] the locations of VLP enrichment do not co-stain with Lysotracker, which is a marker for acidified intracellular compartments, and the VLP enriched spots are often located at the cell periphery (Data not shown). The inventors augmented the VLP tracking with simultaneous spatial mapping of the CD169-mCherry fusion protein and observed strong enrichment of CD169-mCherry at the site of VLP clustering (Data not shown), consistent with a role of CD169 as the receptor for HIV Gag VLPs.

CD169-Mediated Uptake and Sequestration of GM3 Functionalized AVNs

In the next step, the inventors verified whether GM3 containing AVNs reproduce the observed VLP behavior. Darkfield image of HeLa/CD169 cells after 10 min of incubation with AVN1 particles containing 3% GM3. AVN1 binds efficiently to HeLa/CD169. First, the inventors tested if nanoconjugated GM3 is a ligand for CD169 by quantifying the binding efficacies of GM3 and Gal-Cer containing AVNs and of blank controls. HeLa and HeLa/CD169 cells were incubated with 5×10⁸/mL AVNs in DMEM for 10 min, washed to remove unbound particles, and inspected via darkfield microscopy. AVN2 particles containing 3% GM3 also show efficient binding to HeLa/CD169 under otherwise identical conditions. Interestingly, only GM3 containing AVN1 and AVN2 but not Gal-Cer containing AVN1 or AVN2 bind to HeLa/CD169 cells. GSL-free blank AVN1 or AVN2 also did not bind to HeLa/CD169 cells. (data not shown) In additional control experiments the inventors verified that GM3-containing AVNs do not bind to HeLa cells (data not shown). Together, these observations confirm that GM3 functionalized AVNs bind specifically to CD169.

The inventors included a comparison of the spectral content of AVNs and cellular background by analyzing the relative intensity distribution on the red (R), green (G), and blue (B) color channels of the digital camera used to acquire the cell images. The relative distributions of the red, green and blue color channels in a digital camera for an AVN-bound cell surface and for a control cell surface void of AVNs are shown in FIGS. 3a asd 3b. While the intensity of the cellular background is equally distributed across the R, G, B channels, the relative contributions from the R and G channels are locally increased in areas containing AVNs. The inventors concluded that, due to their spectral characteristics and their high intensity (see insets), AVNs built around an 80 nm Au core can be differentiated with high fidelity even from grainy background in the investigated single cell layer.

The inventors took advantage of the large optical cross-sections of GM3 functionalized AVNs to determine their spatial distribution in HeLa/CD169 cells 20 h after initial AVN binding. GM3 containing AVNs sequester in peripheral cellular regions in HeLa/CD169 cells. Darkfield images of HeLa/CD169 cells 20 h after an initial 10 min exposure to GM3 containing AVN1 or AVN2. Corresponding fluorescence images of HeLa/CD169 with GM3 containing AVN2 after nucleus (observed as blue) and Lysotracker (observed as red) staining. The images of representative cells from five independent experiments were analyzed. Overlaid darkfield and fluorescence Lysotracker images of HeLa/CD169 cells after 4 h of incubation with EGF functionalized 80 nm Au NPs, 20 h after incubation with pegylated 80 nm Au NPs, or 20 h after 10 min incubation with fluorescently labeled GM3-liposomes were analyzed. The AVNs show an enrichment in regions that do not co-stain with the Lysotracker. Overlay of the darkfield with the CD169-mCherry fluorescent image of GM3-AVN2 on HeLa/CD169-mCherry cells 20 h after incubation confirms an increased CD169 concentrations at locations of AVN2 enrichment. These experiments revealed a characteristic spatial redistribution of the AVNs from an initial random distribution to a preferential spatial enrichment in discrete spots at the cell periphery. The representative darkfield images of GM3 containing AVN1 and AVN2 treated HeLa/CD169 cells acquired 20 h after AVN exposure illustrate the formation of distinct NP clusters at the cell periphery. In the case of AVN2 we also performed fluorescence staining experiments to image the acidified membrane compartments and the cell nucleus (data not shown). The correlated darkfield/fluorescence images reveal that the locations of high AVN concentration do not co-localize with Lysotracker. The preferential localization of AVN clusters at the HeLa/CD169 cell periphery in Lysotracker negative compartments excludes conventional lysosomal compartments as origin of the large-scale AVN clustering, similar to the localization pattern observed with HIV Gag-eGFP VLPs. As in the case of the VLPs, we observed this phenotype in approximately ⅓ of all investigated cells. We attribute the variability in the cellular response to AVNs and VLPs to the intrinsic heterogeneity of immortalized cancer cell lines,[58,59] as well as to variations in the CD169 expression level on the single cell level. The observation of similar spatio-temporal distributions for both AVN1 and AVN2 implies that the intact lipid bilayer membrane of AVN1 is not required to trigger GM3-CD169-mediated cellular processes, but that the presentation of GM3 in a single leaflet tethered to a solid core, as is the case for AVN2, is sufficient to successfully reproduce HIV Gag VLP behavior in HeLa/CD169 cells.

The inventors correlated AVN clustering with the spatial CD169 distribution through combination of darkfield and fluorescence microscopy in HeLa cells expressing CD169-mCherry fusion protein. Analogous to the co-localization of CD169 with HIV Gag-eGFP VLPs, the overlay of darkfield and fluorescence images in above experiment reveals an enrichment of CD169 at the sites of AVN clustering. The co-clustering of AVNs and CD169 20 h after AVN binding implies that GM3 remains associated with the NPs after binding to the cell. The demonstration of CD169-dependent binding and spatial clustering of AVNs confirms a successful reproduction of the HIV Gag VLP behavior in HeLa/CD169. Since GM3 is the only ligand on the AVN surface, and because the non-specific binding of AVNs without GM3 is negligible, the successful reverse engineering of HIV Gag VLPs with AVNs provides direct experimental evidence that GM3~CD169 binding interactions are responsible for triggering the cellular response that culminates in the observed spatial sequestration of HIV Gag VLPs and AVNs.

The inventors also emphasize that the spatial redistribution observed for GM3-functionalized AVNs cannot be attributed to a general cellular response to non-degradable inorganic nanomaterials. The spatial sequestration of AVNs is strikingly different from what is typically observed for NPs that undergo conventional endocytosis.[60] Epidermal growth factor (EGF) functionalized NPs, which target the endocytic EGF receptor, as well as pegylated NP, are collected in perinuclear, acidified compartments. Due to the long time gap of 20 h between AVN exposure and analysis of AVN distribution, the inventors can also exclude the possibility that intermediate endocytosis states are observed for the GM3 containing AVNs. Instead, the unique spatial distribution of the AVNs corroborates the hypothesis that GM3-CD169 binding elicits a distinct cellular response different from conventional endocytosis. Interestingly, this behavior was found to be specific to AVNs, while GM3 containing liposomes of identical composition were exclusively collected in lysosomal compartments (data not shown). This difference between the soft liposomes and the stiffer, metal core containing AVNs indicates a role of the mechanical properties in determining the intracellular fate of virus particles.

Although HeLa/CD169 cells are a useful model system to test and calibrate AVNs, it is unclear to what degree the observed spatial segregation of AVNs in HeLa/CD169 cells is relevant in DCs that mediate HIV-1 trans-infection. To clarify this question, primary monocyte derived DCs were matured with *E. coli* lipopolysaccharides (LPS) and then incubated with AVNs. While binding of Gal-Cer or blank AVNs to mature DCs was very low (data not shown), GM3 containing AVNs bound efficiently to mature DCs. The inventors studied the darkfield and fluorescence images of mature DCs that were continuously incubated with GM3 containing AVN1 for 1 h under culture conditions similar to those for HeLa/CD169 cells. The inventors observed that GM3-AVNs captured by mature DCs were redistributed and collected in tightly focused spatial locations. For mature DCs, 1 h of incubation with AVNs was sufficient to result in a strongly polarized AVN distribution with large NP clusters preferentially located at the cell periphery (data not shown). Darkfield and fluorescent Lysotracker costaining experiments (data not shown) confirm that the AVN enriched compartments in mature DCs are distinct from lysosomal compartments since no colocalization was observed between AVNs and lysosomal marker. While in HeLa/CD169 cells, multiple smaller AVN clusters are frequently found within a single cell, in mature DCs we preferentially observed the formation of one single compartment highly enriched in AVNs. Although the data obtained with both mature DCs and HeLa/CD169 cells confirm the existence of a cellular process that results in a spatial coalescence of bound AVNs, CD169-mediated trafficking and localization of AVNs in peripheral non-lysosomal compartments occurs with faster kinetics and is more pronounced in mature DCs.

The inventors correlated the spatial distributions of VLPs and AVNs in mature DCs through combined fluorescence and darkfield microscopy after 1 h of incubation. The inventors found that the regions enriched in VLPs and AVNs show an almost perfect colocalization (data not shown), confirming that both VLPs and AVNs are sequestered into identical compartments. Previous studies have demonstrated that cellular compartments containing infectious HIV-1 particles in mature DCs are enriched in tetraspanins.[61,62] The inventors immunolabeled the tetraspanin CD81 and imaged its distribution through fluorescence microscopy. These experiments revealed an unambiguous association of CD81 with AVN containing compartments (data not shown).

Localization of Peripheral AVNs in HeLa/CD169 Cells Through FIB/SEM

The multimodal Au core of AVNs makes it possible to investigate the peripheral accumulation of AVNs observed in the optical microscope via scanning electron microscopy (SEM) and focused ion beam (FIB) milling.[63] SEM detects the secondary electrons generated upon impact from a primary electron beam. Since the secondary electrons have a very short escape depth,[64] SEM imaging is highly surface specific. Optical darkfield and correlated SEM images of representative HeLa/CD169 cells 20 h after addition of AVN2 were observed (data not shown). The optical image indicates a large number of bound AVNs and their clustering in a peripheral cell area. Prior to any FIB milling the number of detected NPs in this area is low, and those NPs that are detected are located right at the cell edge where the cell is very thin (data not shown). To obtain further information about the relative localization of the AVN clusters with regard to the cell membrane, we removed cellular material through FIB milling in the area under investigation. At magnified view show that already after the removal of only 10 nm of cellular material, additional AVN clusters as well as individual AVNs become detectable in areas that did not contain NPs. Some clusters are only faintly visible, indicating that they are still mostly contained in the cell matrix. An additional milling of 60 nm further excavates the large AVN clusters (data not shown). A tilted view (52°) of the area after removal of approximately 90 nm of cellular material. When the inventors milled even deeper, the AVNs were gradually removed and no additional AVNs were observed in the investigated cell section.

The picture that emerges from the combined optical and electron microscopic characterization is that, in HeLa/CD169 cells, the GM3-CD169-mediated AVN sequestration at the cell periphery leads to localization of AVN clusters within tens of nanometers below the plasma membrane. At the very edge of the cell, where the cell is thinnest, the AVNs can be located directly on the cell surface. The observation of AVN enrichment close to the membrane in HeLa/CD169 cells warrants additional future studies into the spatial localization of GM3 functionalized AVNs in DCs, where the dynamic range of possible separations between AVNs and plasma membrane is much larger. The inventors studies also indicate that AVNs in combination with SEM/FIB as an invaluable tool in future studies to determine the localization of GM3 functionalized AVNs in DCs.

The references cited herein and throughout the specification are incorporated herein by reference.

REFERENCES

1. Marsh, M. & Helenius, A. Virus entry: open sesame. Cell 124, 729-740(2006).
2. Kwong, P. D. et al. Structure of an HIV gp120 envelope glycoprotein in complex with the CD4 receptor and a neutralizing human antibody. Nature 393, 648-659 (1998).
3. Wu, L. & KewalRamani, V. N. Dendritic-cell interactions with HIV: infection and viral dissemination. Nat Rev Immunol 6, 859-868 (2006).
4. Dong, C., Janas, A. M., Wang, J. H., Olson, W. J. & Wu, L. Characterization of human immunodeficiency virus type 1 replication in immature and mature dendritic cells reveals dissociable cis- and trans-infection. J Virol 81, 11352-11362 (2007).
5. Waheed, A. A. & Freed, E. O. The Role of Lipids in Retrovirus Replication. Viruses 2, 1146-1180 (2010).
6. Gummuluru, S., Rogel, M., Stamatatos, L. & Emerman, M. Binding of human immunodeficiency virus type 1 to immature dendritic cells can occur independently of DC-SIGN and mannose binding C-type lectin receptors in a cholesterol dependent manner. J Virol 77, 12865-12874 (2003).
7. Izquierdo-Useros, N. et al. Capture and transfer of HIV-1 particles by mature dendritic cells converges with the exosome-dissemination pathway. Blood 113, 2732-2741 (2009).

8. Puryear, W. B., Yu, X. W., Ramirez, N. P., Reinhard, B. M. & Gummuluru, S. HIV-1 incorporation of host-cell-derived glycosphingolipid GM3 allows for capture by mature dendritic cells. P Natl Acad Sci USA 109, 7475-7480 (2012).
9. Izquierdo-Useros, N. et al. Sialyllactose in Viral Membrane Gangliosides Is a Novel Molecular Recognition Pattern for Mature Dendritic Cell Capture of HIV-1. PLoS biology 10 (2012).
10. Izquierdo-Useros, N. et al. Maturation of blood-derived dendritic cells enhances human immunodeficiency virus type 1 capture and transmission. J Virol 81, 7559-7570 (2007).
11. Hatch, S. C., Archer, J. & Gummuluru, S. Glycosphingolipid Composition of Human Immunodeficiency Virus Type 1 (HIV-1) Particles Is a Crucial Determinant for Dendritic Cell-Mediated HIV-1 trans-Infection. J Virol 83, 3496-3506 (2009).
12. Puryear, W. B. & Gummuluru, S. Role of glycosphingolipids in dendritic cell-mediated HIV-1 trans-infection. Adv Exp Med Biol 762, 131-153 (2013).
13. Puryear, W. B. et al. Interferon-inducible mechanism of dendritic cell-mediated HIV-1 dissemination is dependent on Siglec-1/CD169. PLoS pathogens 9, e1003291 (2013).
14. Nap, R. J. & Szleifer, I. How to Optimize Binding of Coated Nanoparticles: Coupling of Physical Interactions, Molecular Organization and Chemical State. Biomater Sci 1, 814-823 (2013).
15. Seisenberger, G. et al. Real-time single-molecule imaging of the infection pathway of an adeno-associated virus. Science 294, 1929-1932 (2001).
16. Brandenburg, B. & Zhuang, X. W. Virus trafficking—learning from single-virus tracking. Nat Rev Microbiol 5, 197-208 (2007).
17. Kukura, P. et al. High-speed nanoscopic tracking of the position and orientation of a single virus. Nat Methods 6, 923-927, doi:10.1038/nmeth.1395 (2009).
18. Ashley, C. E. et al. The targeted delivery of multicomponent cargos to cancer cells by nanoporous particle-supported lipid bilayers. Nat Mater 10, 389-397 (2011).
19. Mastrobattista, E., van der Aa, M. A., Hennink, W. E. & Crommelin, D. J. Artificial viruses: a nanotechnological approach to gene delivery. Nat Rev Drug Discov 5, 115-121 (2006).
20. Goicochea, N. L. et al. Structure and stoichiometry of template-directed recombinant HIV-1 Gag particles. J Mol Biol 410, 667-680 (2011).
21. Manchester, M. & Singh, P. Virus-based nanoparticles (VNPs): platform technologies for diagnostic imaging. Adv. Drug Delivery Rev 58, 1505-1522 (2006).
22. Willis, S. et al. Virus-like particles as quantitative probes of membrane protein interactions. Biochemistry 47, 6988-6990 (2008).
23. Thaxton, C. S., Daniel, W. L., Giljohann, D. A., Thomas, A. D. & Mirkin, C. A. Templated Spherical High Density Lipoprotein Nanoparticles. J Am Chem Soc 131, 1384-1385 (2009).
24. Aniagyei, S. E., Dufort, C., Kao, C. C. & Dragnea, B. Self-assembly approaches to nanomaterial encapsulation in viral protein cages. J Mater Chem 18, 3763-3774 (2008).
25. Torchilin, V. P. Recent advances with liposomes as pharmaceutical carriers. Nat Rev Drug Discov 4, 145-160 (2005).
26. Chen, W. H. C. et al. Antigen Delivery to Macrophages Using Liposomal Nanoparticles Targeting Sialoadhesin/CD169. Plos One 7 (2012).
27. Nycholat, C. M., Rademacher, C., Kawasaki, N. & Paulson, J. C. In silico-aided design of a glycan ligand of sialoadhesin for in vivo targeting of macrophages. J Am Chem Soc 134, 15696-15699 (2012).
28. Sharma, R., Ghasparian, A., Robinson, J. A. & McCullough, K. C. Synthetic virus-like particles target dendritic cell lipid rafts for rapid endocytosis primarily but not exclusively by macropinocytosis. Plos One 7, e43248 (2012).
29. Vieweger, M., Goicochea, N., Koh, E. S. & Dragnea, B. Photothermal imaging and measurement of protein shell stoichiometry of single HIV-1 Gag virus-like nanoparticles. ACS nano 5, 7324-7333 (2011).
30. Gross, I. et al. A conformational switch controlling HIV-1 morphogenesis. The EMBO J 19, 103-113 (2000).
31. Campbell, S. et al. Modulation of HIV-like particle assembly in vitro by inositol phosphates. Proc Natl Acad Sci USA 98, 10875-10879 (2001).
32. Datta, S. A. & Rein, A. Preparation of recombinant HIV-1 gag protein and assembly of virus-like particles in vitro. Meth Mol Biol 485, 197-208 (2009).
33. Zeltins, A. Construction and characterization of virus-like particles: a review. Mol Biotechnol 53, 92-107 (2013).
34. Briggs, J. A., Wilk, T., Welker, R., Krausslich, H. G. & Fuller, S. D. Structural organization of authentic, mature HIV-1 virions and cores. The EMBO J 22, 1707-1715 (2003).
35. Gentile, M. et al. Determination of the size of HIV using adenovirus type 2 as an internal length marker. J Virol Methods 48, 43-52 (1994).
36. Ganser-Pornillos, B. K., Yeager, M. & Pornillos, O. Assembly and architecture of HIV. Adv Exp Med Biol 726, 441-465 (2012).
37. Ganser-Pornillos, B. K., Yeager, M. & Sundquist, W. I. The structural biology of HIV assembly. Curr Opin Struc Biol 18, 203-217 (2008).
38. Nel, A. E. et al. Understanding biophysicochemical interactions at the nano-bio interface. Nat Mater 8, 543-557 (2009).
39. Kol, N. et al. A stiffness switch in human immunodeficiency virus. Biophys J 92, 1777-1783 (2007).
40. Murphy, C. J. et al. Gold nanoparticles in biology: beyond toxicity to cellular imaging. Acc Chem Res 41, 1721-1730 (2008).
41. Wu, L. & Reinhard, B. M. Probing Subdiffraction Limit Separations with Plasmon Coupling Microscopy: Concepts and Applications. Chem Soc Rev DOI: 10.1039/C3CS60340G (2014).
42. Kreibig, U. & Vollmer, M. Optical Properties of Metal Clusters. (Springer, 1995).
43. Yguerabide, J. & Yguerabide, E. E. Light-scattering submicroscopic particles as highly fluorescent analogs and their use as tracer labels in clinical and biological applications—II. Experimental characterization. Anal Biochem 262, 157-176 (1998).
44. Schultz, S., Smith, D. R., Mock, J. J. & Schultz, D. A. Single-target molecule detection with nonbleaching multicolor optical immunolabels. Proc Natl Acad Sci USA 97, 996-1001 (2000).
45. Yang, J. A. & Murphy, C. J. Evidence for Patchy Lipid Layers on Gold Nanoparticle Surfaces. Langmuir 28, 5404-5416 (2012).
46. Ip, S., MacLaughlin, C. M., Gunari, N. & Walker, G. C. Phospholipid Membrane Encapsulation of Nanoparticles for Surface-Enhanced Raman Scattering. Langmuir 27, 7024-7033 (2011).

47 Bakshi, M. S., Possmayer, F. & Peterson, N. O. Role of Different Phospholipids in the Synthesis of Pearl-Necklace-Type Gold-Silver Bimetallic Nanoparticles as Bioconjugate Materials. J Phys Chem C 111, 14113-14124 (2007).

48 Lee, S. E. et al. Biologically Functional Cationic Phospholipid-Gold Nanoplasmonic Carriers of RNA. J Am Chem Soc 131, 14066-14074 (2009).

49 van Schooneveld, M. M. et al. Improved biocompatibility and pharmacokinetics of silica nanoparticles by means of a lipid coating: A multimodality investigation. Nano Lett 8, 2517-2525 (2008).

50 Chan, R. et al. Retroviruses Human Immunodeficiency Virus and Murine Leukemia Virus Are Enriched in Phosphoinositides. J. Virol. 82, 11228-11238 (2008).

51 Brugger, B. et al. The HIV lipidome: a raft with an unusual composition. Proc Natl Acad Sci USA 103, 2641-2646 (2006).

52 Lai, S. K. et al. Human immunodeficiency virus type 1 is trapped by acidic but not by neutralized human cervicovaginal mucus. J Virol 83, 11196-11200 (2009).

53 Huhn, D. et al. Polymer-coated nanoparticles interacting with proteins and cells: focusing on the sign of the net charge. ACS Nano 7, 3253-3263 (2013).

54 Wang, J., Boriskina, S. V., Wang, H. & Reinhard, B. M. Illuminating Epidermal Growth Factor Receptor Densities on Filopodia through Plasmon Coupling. ACS Nano 5, 6619 (2011).

55 Wang, J., Yu, X., Boriskina, S. V. & Reinhard, B. M. Quantification of Differential ErbB1 and ErbB2 Cell Surface Expression and Spatial Nanoclustering through Plasmon Coupling. Nano Lett 12, 3231-3237 (2012).

56 Wampler, H. P. & Ivanisevic, A. Nanoindentation of gold nanoparticles functionalized with proteins. Micron 44, 444-448 (2009).

57 Liang, X., Mao, G. & Ng, K. Y. Mechanical properties and stability measurement of cholesterol-containing liposome on mica by atomic force microscopy. J Colloid Interface Sci 278, 53-62 (2004).

58 Mittelman, D. & Wilson, J. H. The fractured genome of HeLa cells. Genome Biol 14, 111 (2013).

59 Burdall, S. E., Hanby, A. M., Lansdown, M. R. & Speirs, V. Breast cancer cell lines: friend or foe? Breast Cancer Res 5, 89-95 (2003).

60 Canton, I. & Battaglia, G. Endocytosis at the nanoscale. Chem Soc Rev 41, 2718-2739 (2012).

61 Garcia, E. et al. HIV-1 Trafficking to the Dendritic Cell-T-Cell Infectious Synapse Uses a Pathway of Tetraspanin Sorting to the Immunological Synapse. Traffic 6, 488-501 (2005).

62 Yu, H. J., Reuter, M. A. & McDonald, D. HIV traffics through a specialized, surface-accessible intracellular compartments during trans-infection of T cells by mature dendritic cells. PLoS pathogens 4, e10000134 (2008).

63 Bennett, A. E. et al. Ion-Abrasion Scanning Electron Microscopy Reveals Surface-Connected Tubular Conduits in HIV-Infected Macrophages. PLoS pathogens 5, e1000591 (2009).

64 Ishitani, T. & Tsuboi, H. Objective comparison of scanning ion and scanning electron microscope images. Scanning 19, 489-497 (1997).

65 Izquierdo-Useros, N. et al. HIV and Mature Dendritic Cells: Trojan Exosomes Riding the Trojan Horse. PLoS pathogens 6, e1000740 (2010).

66 Wiley, R. D. & Gummuluru, S. Immature dendritic cell-derived exosomes can mediate HIV-1 trans infection. Proc Natl Acad Sci USA 103, 738-743 (2006).

67 Cavrois, M., Neidleman, J., Kreisberg, J. F. & Greene, W. C. In vitro derived dendritic cells trans-infect CD4 T cells primarily with surface-bound HIV-1 virions. PLoS pathogens 3, e4 (2007).

68 Felts, R. L. et al. 3D visualization of HIV transfer at the virological synapse between dendritic cells and T cells. Proc Natl Acad Sci USA 107, 13336-13341 (2010).

69 Izquierdo-Useros, N. et al. Siglec-1 is a novel dendritic cell receptor that mediates HIV-1 trans-infection through recognition of viral membrane gangliosides. PLoS biology 10, e1001448 (2012).

70 Hartnell, A. et al. Characterization of human sialoahesin, a sialic acid binding receptor expressed by resident and inflammatory macrophage populations. Blood 97, 288-296 (2001).

TABLE 1

Lipid membrane composition of HIV1 and AVN particles in molar percentage.

| | HIV | | AVN1 & AVN2 | | |
|---|---|---|---|---|---|
| | | | AVN-Blank | AVN-Gal-Cer | AVN-GM3 |
| PC | 8.80%[51] | | | | |
| SM&DHSM | 18.4%[51] | DPPC | 54% | 51% | 51% |
| PE&pl-PE | 19.2%[51] | Cholesterol | | 45% | |
| PS | 8.4%[51] | PS | | 1% | |
| Cholesterol | 45.1%[51] | GM3 | 0 | 0 | 3% |
| GM3 | ~1.6%[50] | Gal-Cer | 0 | 3% | 0 |
| | | Topfluor-cholesterol (lipid dye) | | 0.1% | |

Abbreviations: PC = phosphatidylcholine; DHSM = dihydrosphingomyelin; SM = sphingomyelin; PE = phosphatidylethanolamine; pl-PE = plasmaenylethanolamine; PS = phosphatidylserine; DPPC = dipalmitoylphosphatidylcholine. GM3 = monosialodihexosylganglioside; Gal-Cer = galactosylceramide.

What is claimed:

1. A nanoparticle comprising:
   a) a biodegradable core having a largest diameter between 50-90 nm;
   b) a coating layer encasing the biodegradable core, wherein the biodegradable core comprises a material selected from the group consisting of silica, mesoporous silica, polystyrene, titania, polyhydroxyalkanoates, polylactic acid (PLA), polybutylene succinate (PBS), polycaprolactone (PCL), polyanhydrides, polyvinyl alcohol, and cellulose esters; and
   c) a ganglioside GM3-containing mixed lipid layer comprising of dipalmitoylphosphatidylcholine (DPPC), cholesterol, phosphatidylserine (PS), and aNeu5Ac(2-3)bDGalp(1-4)bDGlcp(1-1)Cer (GM3); wherein the ganglioside GM3-mixed lipid layer is exterior of the coating layer and is integrated into the coating layer, and wherein the nanoparticles have an overall particle size between 60-100 nm.

2. The nanoparticle of claim 1, wherein the biodegradable core is a solid core.

3. The nanoparticle of claim 1, wherein the biodegradable core has a shape that is selected from the group consisting of ellipsoid, spherical, rod-like, octahedral, and cube-like.

4. The nanoparticle of claim 1, wherein the coating layer is a thiolated lipid, a silane with long alkyl chains, or polyethylene glycol thiol.

5. The nanoparticle of claim 1, wherein the ganglioside GM3 containing mixed lipid layer consists of 40%-60% of DPPC.

6. The nanoparticle of claim 1, wherein the ganglioside GM3 containing mixed lipid layer consists of 40%-60% of cholesterol.

7. The nanoparticle of claim 1, wherein the ganglioside GM3 containing mixed lipid layer consists of 0.5%-5% of PS.

8. The nanoparticle of claim 1, wherein the ganglioside GM3 containing mixed lipid layer consists of 0.1%-6% of GM3.

9. The nanoparticle of claim 1, wherein the ganglioside GM3 containing mixed lipid layer optionally consist of galactosylceramide (Gal-Cer).

10. The nanoparticle of claim 1, wherein the ganglioside GM3 containing mixed lipid layer consists of DPPC, cholesterol, PS, and GM3, and optionally Gal-Cer.

11. The nanoparticle of claim 1, wherein the nanoparticle comprises a second layer of ganglioside GM3 containing mixed lipid.

12. A method of delivering a nanoparticle into a cell comprising adding a nanoparticle of claim 1 to a CD169-expressing eukaryotic cell under conditions that permit the nanoparticle to be endocytosed into the CD169-expressing eukaryotic cell, and waiting for a sufficient time for endocytosis to occur.

13. The method of claim 12, wherein the CD169-expressing eukaryotic cell is a Hela cell, a dendritic cell or a macrophage.

14. The method of claim 12, wherein the nanoparticle is sequestered within non-lysosomal tetraspanin-positive compartments of the CD169-expressing eukaryotic cell.

15. The nanoparticle of claim 1, wherein the nanoparticle, together with a physiologically acceptable carrier, is formulated as a pharmaceutical composition.

16. A method of making a nanoparticle of claim 1 comprising:

a) contacting a core nanoparticle with a coating layer material to coat the particle;
b) adding the coated core nanoparticle to a ganglioside GM3 containing mixed lipid solution;
c) sonicating the contacted mixture of step (b) for a period of time;
d) extruding the particles from step (c) through a membrane with a pore size of about 100-200 nm; and
e) collecting the extruded nanoparticles from the membrane.

17. A method of studying the interaction between CD169+ dendritic cells or macrophage and CD4+T cells comprising:
a) contacting a CD169+ dendritic cell or macrophage with a nanoparticle of claim 1;
b) allowing the nanoparticle to be taken up into the CD169+ dendritic cell or macrophage;
c) contacting the cell of step b with a CD4+T cells; and
d) observing the interaction between the CD169+ dendritic cell or macrophage and the CD4+T cell.

\* \* \* \* \*

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
atcagggaca ggccatgtcc                                            20

```
<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acctctagac aacaccactg gtccgcccag g                              31

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaaaaatcta gaatggtgag caaggg                                    26

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aacctctaca aatgtggtat gg                                        22
```